United States Patent
Thorpe et al.

(10) Patent No.: US 10,527,412 B2
(45) Date of Patent: Jan. 7, 2020

(54) GAS-MAPPING 3D IMAGER MEASUREMENT TECHNIQUES AND METHOD OF DATA PROCESSING

(71) Applicant: Bridger Photonics, Inc., Bozeman, MT (US)

(72) Inventors: Michael Thorpe, Bozeman, MT (US); Aaron Kreitinger, Bozeman, MT (US); Stephen Crouch, Bozeman, MT (US)

(73) Assignee: Bridger Photonics, Inc., Bozeman, MT (US)

( * ) Notice: Subject to any disclaimer, the term of this patent is extended or adjusted under 35 U.S.C. 154(b) by 216 days.

(21) Appl. No.: 15/285,787

(22) Filed: Oct. 5, 2016

(65) Prior Publication Data

US 2017/0097274 A1   Apr. 6, 2017

Related U.S. Application Data

(60) Provisional application No. 62/237,992, filed on Oct. 6, 2015.

(51) Int. Cl.
*G01B 21/20* (2006.01)
*G01M 3/28* (2006.01)
(Continued)

(52) U.S. Cl.
CPC ............. *G01B 21/20* (2013.01); *G01C 15/00* (2013.01); *G01M 3/28* (2013.01); *G01M 3/38* (2013.01);
(Continued)

(58) Field of Classification Search
USPC ..................................................... 250/338.5
See application file for complete search history.

(56) References Cited

U.S. PATENT DOCUMENTS 3,925,666 A * 12/1975 Allan ...................... F17C 13/12
250/338.5
4,167,329 A    9/1979 Jelalian et al.
(Continued)

FOREIGN PATENT DOCUMENTS

WO    2010127151 A2    11/2010
WO    2014088650 A1    6/2014
(Continued)

OTHER PUBLICATIONS

U.S. Appl. No. 15/936,247, titled "High-Sensitivity Gas-Mapping 3D Imager and Method of Operation", filed Mar. 26, 2018, pp. all.
(Continued)

*Primary Examiner* — Lam S Nguyen
(74) *Attorney, Agent, or Firm* — Dorsey & Whitney LLP

(57) ABSTRACT

Measurement approaches and data analysis methods are disclosed for combining 3D topographic data with spatially-registered gas concentration data to increase the efficiency of gas monitoring and leak detection tasks. Here, the metric for efficiency is defined as reducing the measurement time required to achieve the detection, or non-detection, of a gas leak with a desired confidence level. Methods are presented for localizing and quantifying detected gas leaks. Particular attention is paid to the combination of 3D spatial data with path-integrated gas concentration measurements acquired using remote gas sensing technologies, as this data can be used to determine the path-averaged gas concentration between the sensor and points in the measurement scene. Path-averaged gas concentration data is useful for finding and quantifying localized regions of elevated (or anomalous) gas concentration making it ideal for a variety of applications including: oil and gas pipeline monitoring, facility leak and emissions monitoring, and environmental monitoring.

11 Claims, 10 Drawing Sheets

(51) Int. Cl.
*G01M 3/38* (2006.01)
*G01N 21/53* (2006.01)
*G01P 5/00* (2006.01)
*G06K 9/00* (2006.01)
*G01C 15/00* (2006.01)
*G01N 21/39* (2006.01)
*G01N 21/17* (2006.01)

(52) U.S. Cl.
CPC ............ *G01N 21/39* (2013.01); *G01N 21/53* (2013.01); *G01P 5/00* (2013.01); *G06K 9/00201* (2013.01); *G01N 2021/1793* (2013.01); *G01N 2021/1795* (2013.01)

(56) References Cited

U.S. PATENT DOCUMENTS

| | | | |
|---|---|---|---|
| 4,593,368 | A | 6/1986 | Fridge et al. |
| 4,795,253 | A * | 1/1989 | Sandridge ................. G01J 3/02 250/338.5 |
| 4,830,486 | A | 5/1989 | Goodwin |
| 5,115,468 | A | 5/1992 | Asahi et al. |
| 5,294,075 | A | 3/1994 | Vertatschitsch et al. |
| 5,367,399 | A | 11/1994 | Kramer |
| 5,371,587 | A | 12/1994 | De Groot et al. |
| 5,534,993 | A | 7/1996 | Ball et al. |
| 5,548,402 | A | 8/1996 | Nogiwa |
| 5,768,001 | A | 6/1998 | Kelley et al. |
| 5,859,694 | A | 1/1999 | Galtier et al. |
| 6,034,976 | A | 3/2000 | Mossberg et al. |
| 6,516,014 | B1 | 2/2003 | Sellin et al. |
| 6,822,742 | B1 | 11/2004 | Kalayeh et al. |
| 6,864,983 | B2 | 3/2005 | Galle et al. |
| 7,215,413 | B2 | 5/2007 | Soreide et al. |
| 7,292,347 | B2 | 11/2007 | Tobiason et al. |
| 7,511,824 | B2 | 3/2009 | Sebastian et al. |
| 7,742,152 | B2 | 6/2010 | Hui et al. |
| 7,920,272 | B2 | 4/2011 | Sebastian et al. |
| 8,010,300 | B1 | 8/2011 | Stearns et al. |
| 8,121,798 | B2 | 2/2012 | Lippert et al. |
| 8,175,126 | B2 | 5/2012 | Rakuljic et al. |
| 8,294,899 | B2 | 10/2012 | Wong |
| 8,582,085 | B2 | 11/2013 | Sebastian et al. |
| 8,730,461 | B2 | 5/2014 | Andreussi |
| 8,781,755 | B2 | 7/2014 | Wong |
| 8,913,636 | B2 | 12/2014 | Roos et al. |
| 9,030,670 | B2 | 5/2015 | Warden et al. |
| 9,559,486 | B2 | 1/2017 | Roos et al. |
| 9,696,423 | B2 | 7/2017 | Martin |
| 9,759,597 | B2 | 9/2017 | Wong |
| 9,784,560 | B2 | 10/2017 | Thorpe et al. |
| 9,864,060 | B2 | 1/2018 | Sebastian et al. |
| 9,970,756 | B2 | 5/2018 | Kreitinger et al. |
| 10,247,538 | B2 | 4/2019 | Roos et al. |
| 2002/0071122 | A1* | 6/2002 | Kulp ........................ G01M 3/38 356/437 |
| 2003/0043437 | A1 | 3/2003 | Stough et al. |
| 2004/0105087 | A1 | 6/2004 | Gogolla et al. |
| 2005/0078296 | A1 | 4/2005 | Bonnet |
| 2005/0094149 | A1 | 5/2005 | Cannon |
| 2006/0050270 | A1 | 3/2006 | Elman |
| 2006/0162428 | A1* | 7/2006 | Hu .......................... G01M 3/20 73/40.7 |
| 2006/0203224 | A1 | 9/2006 | Sebastian et al. |
| 2008/0018881 | A1 | 1/2008 | Hui et al. |
| 2008/0018901 | A1 | 1/2008 | Groot |
| 2009/0046295 | A1 | 2/2009 | Kemp et al. |
| 2009/0153872 | A1 | 6/2009 | Sebastian et al. |
| 2009/0257622 | A1* | 10/2009 | Wolowelsky ......... G01N 21/3518 382/103 |
| 2010/0007547 | A1 | 1/2010 | D'Addio |
| 2010/0091278 | A1 | 4/2010 | Liu et al. |
| 2010/0131207 | A1 | 5/2010 | Lippert et al. |
| 2011/0069309 | A1 | 3/2011 | Newbury et al. |
| 2011/0164783 | A1 | 7/2011 | Hays et al. |
| 2011/0205523 | A1 | 8/2011 | Rezk et al. |
| 2011/0213554 | A1 | 9/2011 | Archibald et al. |
| 2011/0273699 | A1 | 11/2011 | Sebastian et al. |
| 2011/0292403 | A1 | 12/2011 | Jensen et al. |
| 2012/0106579 | A1 | 5/2012 | Roos et al. |
| 2012/0293358 | A1 | 11/2012 | Itoh |
| 2013/0104661 | A1 | 5/2013 | Klotz et al. |
| 2014/0002639 | A1 | 1/2014 | Cheben et al. |
| 2014/0036252 | A1 | 2/2014 | Amzajerdian et al. |
| 2014/0139818 | A1 | 5/2014 | Sebastian et al. |
| 2014/0204363 | A1 | 7/2014 | Slotwinski et al. |
| 2015/0019160 | A1 | 1/2015 | Thurner et al. |
| 2015/0185313 | A1 | 7/2015 | Zhu |
| 2015/0355327 | A1 | 12/2015 | Goodwin et al. |
| 2016/0123718 | A1 | 5/2016 | Roos et al. |
| 2016/0123720 | A1 | 5/2016 | Thorpe et al. |
| 2016/0202225 | A1 | 7/2016 | Feng et al. |
| 2016/0259038 | A1 | 9/2016 | Retterath et al. |
| 2016/0261091 | A1 | 9/2016 | Santis et al. |
| 2017/0097302 | A1 | 4/2017 | Kreitinger et al. |
| 2017/0115218 | A1 | 4/2017 | Huang et al. |
| 2017/0131394 | A1 | 5/2017 | Roger et al. |
| 2017/0146335 | A1 | 5/2017 | Martinez et al. |
| 2017/0191898 | A1 | 7/2017 | Rella et al. |
| 2017/0343333 | A1 | 11/2017 | Thorpe et al. |
| 2018/0188369 | A1 | 7/2018 | Sebastian et al. |
| 2018/0216932 | A1 | 8/2018 | Kreitinger et al. |
| 2019/0170500 | A1 | 6/2019 | Roos et al. |

FOREIGN PATENT DOCUMENTS

| | | |
|---|---|---|
| WO | 2016064897 A1 | 4/2016 |
| WO | 2017187510 A1 | 11/2017 |
| WO | 2019060901 A1 | 3/2019 |
| WO | 2019070751 A1 | 4/2019 |
| WO | 2019079448 A1 | 4/2019 |
| WO | 2019099567 | 5/2019 |

OTHER PUBLICATIONS

PCT Application No. PCT/US18/52682 titled "Digitization Systems and Techniques and Examples of Use in FMCW LIDAR Methods and Apparatuses" filed Sep. 25, 2018, pp. all.

PCT Application No. PCT/US2018/54016, titled "Processing Temporal Segments of Laser Chirps and Examples of Use in FMCW LIDAR Methods anf Apparatuses" filed on Oct. 2, 2018, pp. all.

PCT Application No. PCT/US2018/56285 titled "Apparatuses and Methods for a Rotating Optical Reflector" filed on Oct. 17, 2018, pp. all.

Iiyama, et al., "Linearizing Optical Frequency-Sweep of a Laser Diode for FMCW Reflectrometry", Iiyama et al. Journal of Lightwave Technology, vol. 14, No. 2, Feb. 1996.

Karlsson, et al. "Linearization of the frequencysweep of a frequency-modulated continuous-wave semiconductor laser radar and the resulting ranging performance", Christer J. Karlsson et al, Applied Optics, vol. 38, No. 15, May 20, 1999, pp. 3376-3386.

Roos, et al. "Ultrabroadband optical chirp linearization for precision metrology applications", Optics Letters, vol. 34, Issue 23, pp. 3692-3694 (2009).

Sheen, et al., Sheen, D. M. "Frequency Modulation Spectroscopy Modeling for Remote Chemical Detection." PNNL 13324 (Sep. 2000).

Sivananthan, Integrated Linewidth Reduction of Rapidly Tunable Semiconductor Lasers Sivananthan, Abirami, Ph.D., University of California, Santa Barbara, 2013, 206; 3602218, pp. all.

Iseki, et al., "A Compact Remote Methane Sensor using a Tunable Diode Laser", Meas. Sci. Technol., 11, 594, pp. 217-220 (Jun. 2000).

Lu, et al., "Differential wavelength-scanning heterodyne interferometer for measuring large step height", Applied Optics, vol. 41, No. 28, Oct. 1st, 2002.

U.S. Appl. No. 15/285,550, entitled "High-Sensitivity Gas-Mapping 3D Imager and Method of Operation", filed Oct. 5, 2016.

Amann, et al., "Laser ranging: a critical review of usual techniques for distance measurement," Optical Engineering, vol. 40(1) pp. 10-19 (Jan. 2001).

(56) References Cited

OTHER PUBLICATIONS

Barber, et al., "Accuracy of Active Chirp Linearization for Broadband Frequency Modulated Continuous Wave Ladar," Applied Optics, vol. 49, No. 2, pp. 213-219 (Jan. 2010).
Barker, , "Performance enhancement of intensity-modulated laser rangefinders on natural surfaces", SPIE vol. 5606, pp. 161-168 (Dec. 2004).
Baumann, et al., "Speckle Phase Noise in Coherent Laser Ranging: Fundamental Precision Limitations," Optical Letters, vol. 39, Issue 16, pp. 4776-4779 (Aug. 2014).
Boashash, "Estimating and Interpreting the Instantaneous Frequency of a Signal—Part 2: Algorithms and Applications", Proceedings of the IEE, vol. 80, No. 4, pp. 540-568 (Apr. 1992).
Bomse, et al., "Frequency modulation and wavelength modulation spectroscopies: comparison of experimental methods using a lead-salt diode laser", Appl. Opt., 31, pp. 718-731 (Feb. 1992).
Choma, et al., "Sensitivity Advantage of Swept Source and Fourier Domain Optical Coherence Tomography," Optical Express, vol. 11, No. 18, 2183 (Sep. 2003).
Ciurylo, "Shapes of pressure- and Doppler-broadened spectral lines in the core and near wings", Physical Review A, vol. 58 No. 2, pp. 1029-1039 (Aug. 1998).
Dharamsi, "A theory of modulation spectroscopy with applications of higher harmonic detection", J. Phys. D: Appl. Phys 29, pp. 540-549 (Jun. 1995;1996) (Retrieved Jan. 16, 2017).
Fehr, et al.,"Compact Covariance Descriptors in 3D Point Clouds for Object Recognition", 2012 IEEE International Conference on Robotics and Automation, pp. 1793-1798, (May 2012).
Fujima, et al., "High-resolution distance meter using optical intensity modulation at 28 GHz", Meas. Sci, Technol. 9, pp. 1049-1052 (May 1998).
Gilbert, et al., "Hydrogen Cyanide H13C14N Absorption Reference for 1530 nm to 1565 nm Wavelength Calibration—SRM 2519a", NIST Special Publication 260-137 2005 ED, 29 pages, (Aug. 2005).
Jia-Nian, et al., "Etalon effects analysis in tunable diode laser absorption spectroscopy gas concentration detection system based on wavelength modulation spectroscopy", IEEE SOPO, pp. 1-5 (Jul. 2010).
Johnson, et al., "Using Spin-Images for Efficient Object Recognition in Cluttered 3D Scenes", IEEE Transactions on Pattern Analysis and Machine Intelligence, vol. 21, No. 5, 37 pages (Published May 1999).
Karmacharya, et al., "Knowledge guided object detection and indentification in 3D point clouds", SPIE 9528, 952804-952804-13 (Jun. 2015).
Masiyano, et al., "Use of diffuse reflections in tunable diode laser absorption spectroscopy: implications of laser speckle for gas absorption measurements", Appl. Phys. B 90, pp. 279-288 (Feb. 2008).
Ngo, et al., "An isolated line-shape model to go beyond the Voigt profile in spectroscopic databases and radiative transfer codes", Journal of Quantitative Spectroscopy and Radiative Transfer, 129, pp. 89-100 (Nov. 2013).
Olsovsky, et al., "Chromatic Confocal Microscopy for Multi-depth Imaging of Epithelial Tissue," Biomedical Optics Express, vol. 4, No. 5, pp. 732-740 (May 2013).
Paffenholz, "Direct geo-referencing of 3D point clouds with 3D positioning sensors", (Doctoral Thesis), Leibniz Universitat Hannover, 138 pages (Sep. 2012).
Polyanksy, et al., "High-Accuracy CO2 Line Intensities Determined from Theory and Experiment", Physical Review Letters, 114, 5 pages (Jun. 2015).

Rao, "Information and the accuracy attainable in the estimatin of statistical parameters", Bull. Calcutta Math. Soc., 37,pp. 81-89 (1945, reprinted 1992) (Retrieved Jan. 10, 2017).
Riris, et al., "Airborne measurements of atmospheric methane column abundance using a pulsed integrated-path differential absorption lidar", Applied Optics, vol. 51, No. 34, pp. 8296-8305 (Dec. 2012).
Roos, et al., "Ultrabroadband optical chirp linearization for precision metrology application", Optics Letters, vol. 34 No. 23, pp. 3692-3694 (Dec. 2009).
Rothman, et al., "The HITRAN 2008 molecular spectroscopic database", Journal of Quantitative Spectroscopy & Radiative Transfer, 110, pp. 533-572 (Jul. 2009).
Rusu, et al., "Fast Point Feature Histograms (FPFH) for 3D Registration", IEEE Int. Conf. Robot., pp. 3212-3217 (May 2009).
Sandsten, et al., "Volume flow calculations on gas leaks imaged with infrared gas-correlation", Optics Express, vol. 20, No. 18, pp. 20318-20329 (Aug. 2012).
Sheen, "Frequency Modulation Spectroscopy Modeling for Remote Chemical Detection", PNNL 13324, 51 pages (Sep. 2000).
Silver, "Frequency-modulation spectroscopy for trace species detection: theory and comparison among experimental methods", Appl. Opt., vol. 31 No. 6, pp. 707-717 (Feb. 1992).
Sirat, et al., "Conoscopic Holography," Optics Letters, vol. 10, No. 1 (Jan. 1985).
Stone, et al., "Performance Analysis of Next-Generation LADAR for Manufacturing, Construction, and Mobility," NISTIR 7117 (May 2004).
Twynstra, et al., "Laser-absorption tomography beam arrangement optimization using resolution matrices", Applied Optics, vol. 51, No. 29, pp. 7059-7068 (Oct. 2012).
Xi, et al., "Generic real-time uniorm K-space sampling method for high-speed swept-Source optical cohernece tomography", Optics Express, vol. 18, No. 9, pp. 9511-9517 (Apr. 2010).
Zakrevskyy, et al., "Quantitative calibration- and reference-free wavelength modulation spectroscopy", Infrared Physics & Technology, 55, pp. 183-190 (Mar. 2012).
Zhao, et al., "Calibration-free wavelength-modulation spectroscopy based on a swiftly determined wavelength-modulation frequency response function of a DFB laser", Opt. Exp., vol. 24 No. 2, pp. 1723-1733 (Jan. 2016).
Fransson, Karin et al., "Measurements of VOCs at Refineries Using the Solar Occultation Flux Technique", Department of Radio and Space Science, Chalmers University of Technology, 2002, 1-19.
Lenz, Dawn et al., "Flight Testing of an Advanced Airborne Natural Gas Leak Detection System", ITT Industries Space Systems Division, Oct. 2005, all.
Mather, T.A. et al., "A reassessment of current volcanic emissions from the Central American arc with specific examples from Nicaragua", Journal of Volcanology and Geothermal Research, Nov. 2004, 297-311.
Thoma, Eben D. et al., "Open-Path Tunable Diode Laser Absorption Spectroscopy for Acquisition of Fugitive Emission Flux Data", Journal of the Air & Waste Management Association (vol. 55), Mar. 1, 2012, 658-668.
Zhao, Yanzeng et al., "Lidar Measurement of Ammonia Concentrations and Fluxes in a Plume from a Point Source", Cooperative Institute for Research in Environmental Studies, University of Colorado/NOAA (vol. 19), Jan. 2002, 1928-1938.
Emran, Bara J. et al., "Low-Altitude Aerial Methane Concentration Mapping", School of Engineering, The University of British Columbia, Aug. 10, 2017, pp. 1-12.

\* cited by examiner

GAS-MAPPING 3D IMAGER MEASUREMENT TECHNIQUES AND METHOD OF DATA PROCESSING

CROSS REFERENCE TO RELATED APPLICATIONS

This application claims the benefit of provisional U.S. application Ser. No. 62/237,992, filed Oct. 6, 2015, the contents of which are incorporated herein by reference.

STATEMENT REGARDING RESEARCH & DEVELOPMENT

This invention was made with government support under DE-AR0000544 awarded by the Department of Energy. The government has certain rights in the invention.

FIELD OF THE INVENTION

The present invention generally relates to the application of 3D spatial data and gas concentration data to perform gas leak detection and monitoring.

BACKGROUND OF THE INVENTION

Improved gas detection and monitoring technologies are needed for a variety of emerging applications including:
(1) leak detection and quantification for oil and gas and chemical processing infrastructure,
(2) emissions monitoring from landfill and waste treatment facilities,
(3) monitoring and verification for carbon sequestration, and
(4) environmental terrestrial monitoring to better understand the carbon cycle.

Sensor solutions to meet the needs of emerging applications must provide cost effective, large-area, high-sensitivity, and quantitative detection of target gases, and will likely require mobile sensor platforms that incorporate spatial data such as GPS and GIS for spatial-registering, mapping and time-stamping of acquired datasets. For many applications, advanced measurement capabilities such as leak localization and flux estimation are also desired. The invention disclosed herein describes measurement techniques and data analysis methods that can be implemented using combinations of existing 3D topography and gas concentration sensor technologies to meet emerging measurement needs.

Over the past three decades 3D topographical scanning through such means as LiDAR and photogrammetry has become a powerful tool for large-area surveying, mapping and infrastructure monitoring. Recently, the cost of LiDAR and photogrammetric sensors for producing high-quality 3D spatial data have reached a point where the application and prevalence of 3D data has become widespread. Commercially available sensors can now map terrain and infrastructure with several centimeter precision from distances exceeding 1000 feet and at measurement rates exceeding 500,000 points per second. Data acquired with these sensors is used to create several distinct data representations of a measured topographic scene including: point clouds (See, e.g., the Point Cloud Library), digital surface models, and digital elevation models (See, e.g., OpenDEM). The emergence of 3D data types has been accompanied by the development of vast body of image processing software, such as the Point Cloud Library, for rapid and sophisticated exploitation of 3D data. Examples of common processing tasks for 3D point data include organization of the data in an efficiently searchable tree structure, segmentation of like objects within a scene, detection of occluded portions of a scene from a specified viewing location, surface reconstruction, shape detection and identification of objects in a scene (See, e.g., the Point Cloud Library). The combination of high-quality 3D data with these processing and analysis tools has the potential to play an important role in defining new and valuable measurement procedures for gas detection, localization, and quantification tasks.

SUMMARY OF THE INVENTION

A method is provided for reducing the time needed to monitor for gas leaks, comprising: utilizing 3D spatial data to identify regions and/or structures of a scene for gas monitoring and/or regions that may be occluded from view; utilizing the identified regions and/or structures of the scene to determine a gas sensing measurement procedure that exhibits reduced measurement time and/or improved detection confidence compared to a gas sensing measurement procedure created without knowledge of the 3D spatial data of the scene; and utilizing the determined gas sensing measurement procedure to perform gas sensing of a scene.

The gas sensing measurement may be performed using a remote gas sensor.

The determined gas sensing measurement procedure may include occlusion processing of the 3D spatial data.

The identification of the regions and/or structures of the scene may include segmentation of structures or features in the 3D spatial data.

The identification of the regions and/or structures of the scene may include shape detection or feature identification of structures or features in the 3D spatial data.

The determined gas sensing measurement procedure is performed with a mobile gas sensor;

A method is provided of identifying the leak location or leaking component comprising: acquiring new 3D data of a scene or accessing previously acquired 3D data of a scene; acquiring spatially registered gas concentration measurements within a scene or accessing previously acquired spatially registered gas concentration measurements within a scene; and determining a location of a gas leak source by utilizing 3D spatial data of a scene and spatially registered gas concentration measurements within the scene.

The determined gas leak source location may be combined with component location information and/or feature identification algorithms applied to the 3D spatial data to determine a component corresponding to the leak source.

The determined gas leak source location may involve the use of wind data.

The determined gas leak source location may involve occlusion processing of the scene.

Gas sensing measurements from a plurality of viewing locations may be used to improve the determination of a gas leak source location or the location and extent of a gas plume.

A method is provided for quantifying a detected leak comprising: acquiring new 3D data of a scene or accessing previously acquired 3D data of a scene; acquiring spatially registered gas concentration measurements within a scene or accessing previously acquired spatially registered gas concentration measurements; and determining an anomalous gas quantity in the scene that is greater or less than the background gas quantity in the scene.

The determined anomalous gas quantity may be calculated by first subtracting the background path-averaged gas concentration that is either measured or otherwise known to be in the scene from the measured path-averaged gas concentration data to derive path-integrated anomalous gas concentration data, the path-integrated anomalous gas concentration data is then integrated over the spatial coordinates of the measurement scene to determine the anomalous gas quantity.

Gas sensing measurements from a plurality of viewing locations may be used to improve the accuracy of the anomalous gas quantity determination.

A method is provided of quantifying a gas flux comprising: scanning a laser beam across a gas plume; using the scattered light from the scanned laser beam to determine gas concentration at a plurality of locations through the gas plume; determining or assuming wind data near the gas plume; determining a gas flux by utilizing the determined gas concentration and the determined or assumed wind data.

The scanned laser beam may form a boundary that encloses the leak source.

The method may further comprise: performing measurements of a plume from more than one position to determine a location of the plume and to improve the leak rate estimate.

A method is provided of quantifying a detected gas flux comprising: acquiring new range data for a scene or accessing previously acquired range data for a scene; acquiring spatially registered spatially registered path-integrated gas absorption measurements within a scene or accessing previously acquired spatially registered spatially registered path-integrated gas absorption measurements; and determining a gas flux by utilizing range information with a closed-volume scan pattern of spatially registered path-integrated gas absorption measurements.

The closed-volume scan pattern measurement may be performed from more than one position to determine the plume location and improve the leak rate estimate.

A method is provided of determining the position of a gas plume in 3D space comprising: acquiring new range data for a scene or accessing previously acquired range data for a scene from a plurality of viewing locations; acquiring spatially registered path-integrated gas concentration measurements within a scene from a plurality of viewing locations; and determining the location of a gas plume in 3D space by combining the range data with the path-integrated gas concentration data using a tomographic reconstruction algorithm.

BRIEF DESCRIPTION OF THE DRAWINGS

The accompanying figures where like reference numerals refer to identical or functionally similar elements and which together with the detailed description below are incorporated in and form part of the specification, serve to further illustrate an exemplary embodiment and to explain various principles and advantages in accordance with the present invention.

DETAILED DESCRIPTION

Figure 1:
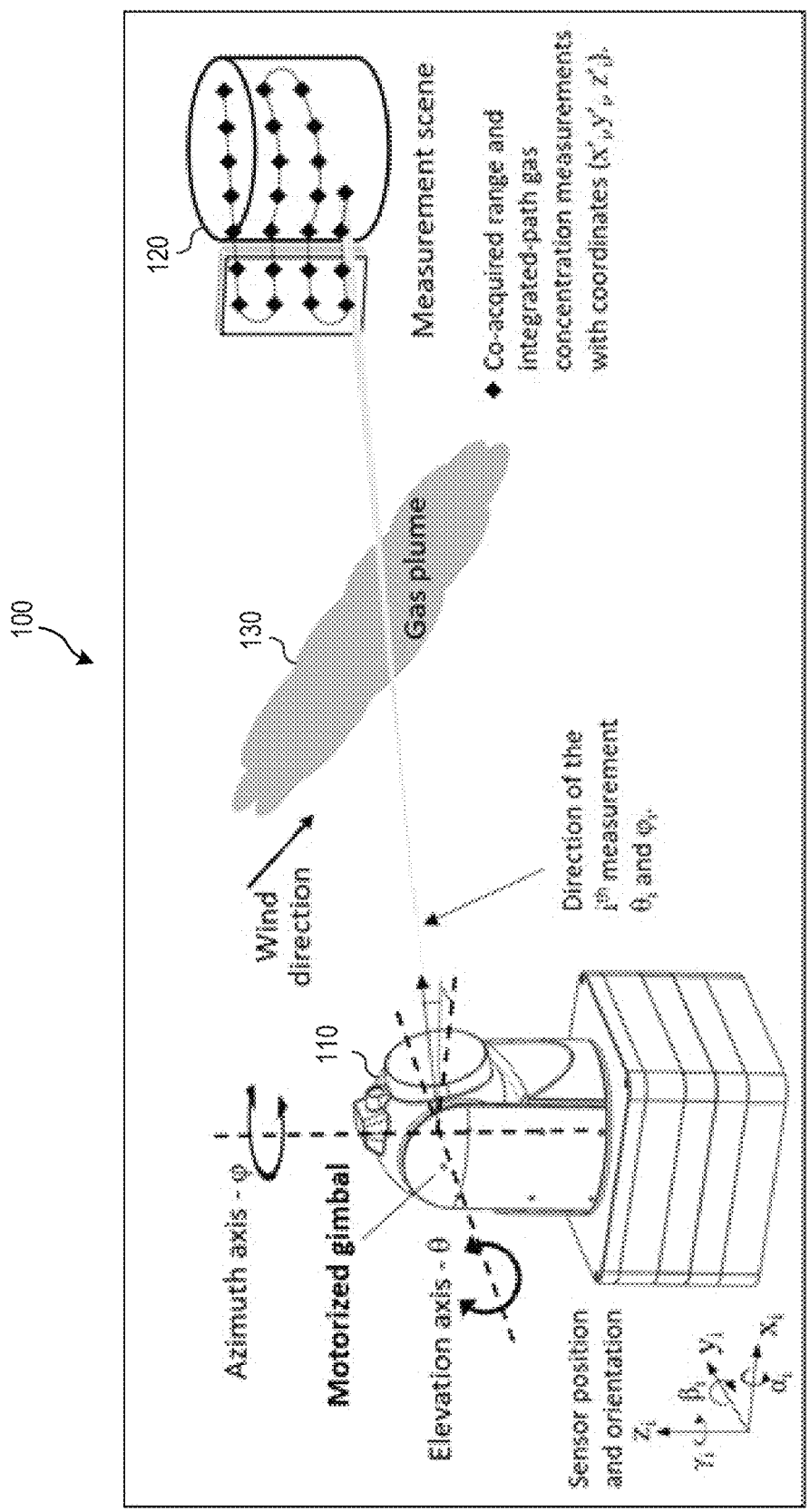
FIG. 1 is a diagram showing an example sensor for measuring spatially-registered target range and gas concentration measurements, according to a disclosed embodiment.

The current disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

1. Overview of Sensor Technologies and Associated Data

In the context of gas leak detection and monitoring, 3D spatial data can be used independent of gas concentration measurements to understand measurement scene and define procedures that minimize measurement time while ensuring a desired level of confidence in the measurement results. Several factors may be considered when defining a good measurement procedure. First, analysis of the 3D data can be used to inform the position (or positions) from which measurements should be made to ensure comprehensive viewing of the measurement scene. As an example, when viewing a scene from only one sensor position, it is possible that a leak source may be occluded from view by structures or topography in the scene. And, depending on the application, it may be critical to ensure that all regions that may contain gas plumes/leaks are sampled with sufficient measurement density to ensure reliable detection. The present disclosure teaches how one may determine the number and location of sensor viewing positions to ensure sensor coverage of a scene to the desired level. Second, the 3D data can be used to assign probabilities for the likelihood of finding leaks as a function of location within the measurement scene. As examples, certain spatial regions of a scene may be more or less prone to leaks based on the infrastructure present in the scene, or certain spatial regions of a scene may contain more expensive or dangerous assets that would represent a greater risk if a leak went undetected. These are two non-limiting examples of spatial regions of a scene that may be more important for monitoring than other spatial regions of the scene. The present disclosure describes how knowledge of the 3D spatial data may allow for the creation of non-uniform gas measurement procedures that reduce the overall measurement time by spending more measurement resources, such as integration time, point density, or averaging, measuring areas of greater importance and less measurement resources on areas of less importance. Furthermore, where it is available, wind data can be included to further improve the probability assignments and provide additional localization of regions of greater importance, such as those with high probability for leak detection. Finally, 3D change detection can be implemented to identify changes in the topography of a scene. If topographic changes are detected, further analysis of the 3D spatial data can be used to rapidly determine if changes to the gas measurement procedure are required for adequate leak detection confidence. Detection of topographic changes can also be used to alert operators to changes in critical infrastructure or their immediate surroundings.

When 3D spatial data is combined with gas concentration measurements several advantages are realized for large-area gas monitoring and leak detection tasks compared to the use of gas concentration measurements alone. This is especially true for path-integrated gas concentration measurements acquired using remote gas sensors based on optical absorption spectroscopy techniques such as wavelength modulation spectroscopy (See, e.g., Bomse, D. S., et. al., "Frequency modulation and wavelength modulation spectroscopies: comparison of experimental methods using a lead-salt diode laser," Appl. Opt., 31, 718-731 (1992)), differential absorption LiDAR (See, e.g., Riris, H., et. al. "Airborne measurements of atmospheric methane column abundance using a pulsed integrated-path differential absorption lidar." Appl. Opt., 51, 34 (2012).), and infrared absorption spectroscopy (See, e.g., the optical gas imager camera offered by FLIR). Using optical absorption spectroscopy the path-integrated concentration of a gas can be inferred by the attenuation of light traveling through the sample according to the Beer-Lambert law, $$P_R = P_T e^{-2\int_0^l \alpha(z) dz} = P_T e^{-2\sigma C_{Pl}} = P_T e^{-2\sigma C_{ave} l}. \qquad (1)$$

Here $P_T$ is the light power transmitted through the gas sample, $P_R$ is the power received by the gas sensor, $\alpha(z)$ is the gas absorption as a function of distance along the measurement path. The path-integrated absorption ($\int_0^l \alpha(z) dz$) can be rewritten to express the laser absorption in terms of the molecular absorption cross section $\sigma$, and either the path-integrated gas concentration $C_{Pl}$, or path-averaged gas concentration $C_{ave}$ and the path length of the gas sample l. For this disclosure the gas sample path length l may also refer to the target range. Furthermore, when not specified the term gas concentration can refer to either the path-integrated or the path averaged gas concentration.

FIG. 1 shows an example sensor 100 for measuring spatially-registered target range and gas concentration measurements. In particular, FIG. 1 is a diagram 100 of an example sensor configuration 110 for acquiring spatially-registered target range to a target 120 and integrated-path gas concentration measurements of a gas plume 130 at measurement scene.

For the present disclosure, range may be considered synonymous with distance. Also, target may be considered synonymous with surface and topographical scatterer. For this example sensor, spatial registration of both range and gas measurements is achieved by overlapping the transmitted range and gas sensing beams while encoders measure the angular positions of both gimbal axes and record the direction of the transmitted beams. This spatial registration enables the reconstruction of gas concentration imagery from collections of individual target range and gas concentration measurements. Gas concentration imagery reconstruction may be further supported by onboard GPS and inertial measurement unit (IMU) sensors that track the sensor position and orientation during measurements. GPS and IMU data may be essential for image reconstruction in mobile sensing applications as the sensor position and orientation can be changing during the measurements. This data may also allow geo-registration of acquired data for both mobile and stationary measurement scenarios. Finally, the compact sensor permits integration onto a variety of mobile platforms including ground-based vehicle, manned aircraft, and unmanned aircraft for large-area and potentially automated measurement procedures.

The first advantage of using 3D spatial data is that knowledge of the distance to remote targets can be combined with path-integrated gas concentration measurements to compute the path-averaged gas concentration ($C_{ave}$) to points in a measurement scene. Measurements of $C_{ave}$ allow for straightforward detection of elevated (or otherwise anomalous) regions of gas concentration in the measurement scene by removing the ambiguity that arises in path-integrated gas concentration measurements between changes in the target range and changes the average gas concentration along the measurement path. The ability to more precisely and less ambiguously detect changes in remote gas concentrations enables leak detection with higher-sensitivity and improved confidence.

For example, the nominal atmospheric concentration of $CO_2$ is currently approximately 400 ppm. To unambiguously attribute a change in the path-integrated gas concentration $C_{PI}$ of the 100 ppm-m to elevated $CO_2$ levels along the measurement path, rather than an increased distance to the topographic target, the distance to the target must be known to better than $\delta R$=100 ppm-m/400 ppm=25 cm. For measurements taken from ranges of tens to hundreds of meters it may be impossible to make such a distinction without a range measurement. Additional benefits of combining 3D spatial data with path-integrated gas concentration measurements include improved leak detection confidence, leak source localization and identification through spatial imaging of gas plumes, quantification of the amount of gas measured in a scene compared to an expected or nominal gas level, the use of shape detection to identify components corresponding to leak sources, and gas flux estimation for detected gas sources or sinks. Finally, wind data can be combined with $C_{ave}$ imagery to improve leak localization, source identification, and flux estimation.

Sections 2 and 3 of this document provide examples and instructions for using 3D spatial data with gas concentration measurements to support increased efficiency and automation of gas detection and monitoring tasks. The process may begin by accessing or acquiring a set of 3 D spatial data that has been collected from multiple perspectives so as to provide full scene coverage. Such a 3D data set could be collected and assimilated in a one-time manner and stored so that subsequent scene visits would benefit from the 3D data on file. Assimilation of 3D spatial data taken from multiple perspectives into a single scene representation can be achieved algorithmically with standard registration algorithms (See, e.g., R. B. Rusu, N. Blodow, and M. Beetz, "Fast Point Feature Histograms (FPFH) for 3D registration," IEEE Int. Conf. Robot., pp. 3212-3217, (2009)), or may be achieved automatically with accurate georeferenced 3D data. With a high-fidelity 3D map of a scene, a gas sensor can begin to exploit the scene features to optimize a variety of gas imaging tasks including: scan time minimization, topographic change detection, leak source localization, leaking component identification, and leak rate quantification. The examples presented here are aimed at detecting leaks in oil and gas production facilities, but the general concepts could be applied to a wide variety of tasks that would benefit from large area and high spatial resolution gas measurements.

2. Leak Detection Measurement Procedure Development Aided by 3D Spatial Data

This section outlines methods for using 3D data to design gas measurement procedures that reduce measurement time while providing quantitative estimates of the confidence of a detection or non-detection event. To begin, consider a "brute force" gas measurement approach where the entirety of the 3D volume must be interrogated, regardless of scene topography, to guarantee full scene analysis. In contrast to the brute force approach, we consider the possibility of "sparse" and "spatially non-uniform" scan approaches. In general, such approaches may assume that the plume resulting from a leak is not isolated but instead has some spatial extent. Thus, an appropriate sparse scan pattern may support leak detection with some likelihood despite under-sampling the volume by design. 3D data can augment such scan approaches so as to better guarantee leak detection.

To highlight the possibilities, consider the effect of occlusion whereby an object hides another object (or volume) from an observer. From a single sensor location, for example, such occluded regions may hide leak sources and thereby prevent the leaks from being detected (false negative result). Or, one may assume that a large number of viewpoints may be needed to reduce occluded regions to an acceptable level. With 3D data, it is possible to determine the number and location of sensor positions to enable efficient coverage of a scene to the desired level. Through analysis of the 3D data, the gas imaging system can take steps to mitigate the effect by altering viewing locations for maximum sparse scan coverage. An example of this concept is shown in FIGS. 2 and 3.

Figure 2:
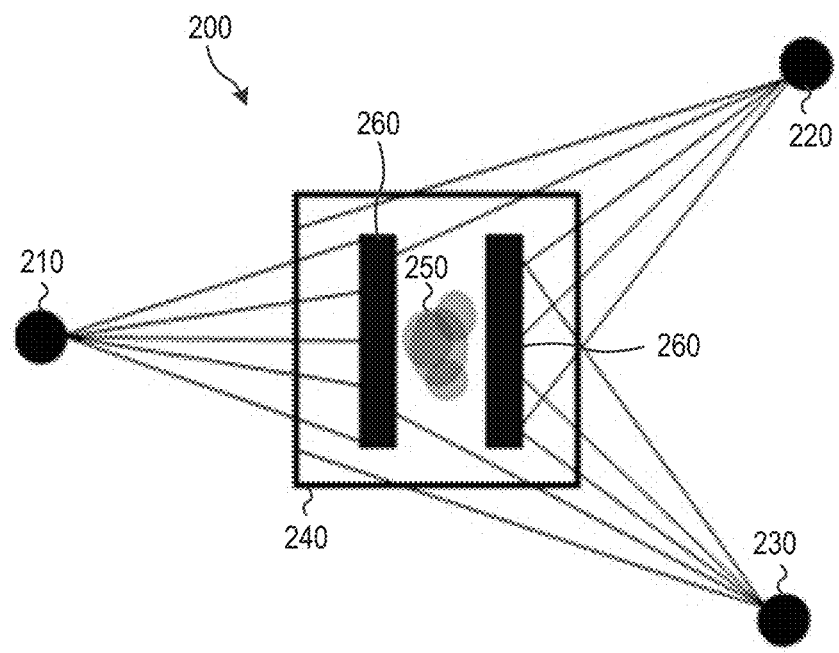
FIG. 2 is an image showing a sparse scan executed from three (3) viewing locations, according to a disclosed embodiment.

FIG. 2 is an image 200 showing a sparse scan executed from three (3) viewing locations 210, 220, 230, according to a disclosed embodiment. Thin black lines represent the integration path of various concentration measurements. Although the pattern should effectively cover the area of interest 240 (black box), the plume 250 (gray) is not interrogated due to the occluding structures 260 (vertical black bars).

Figure 3:
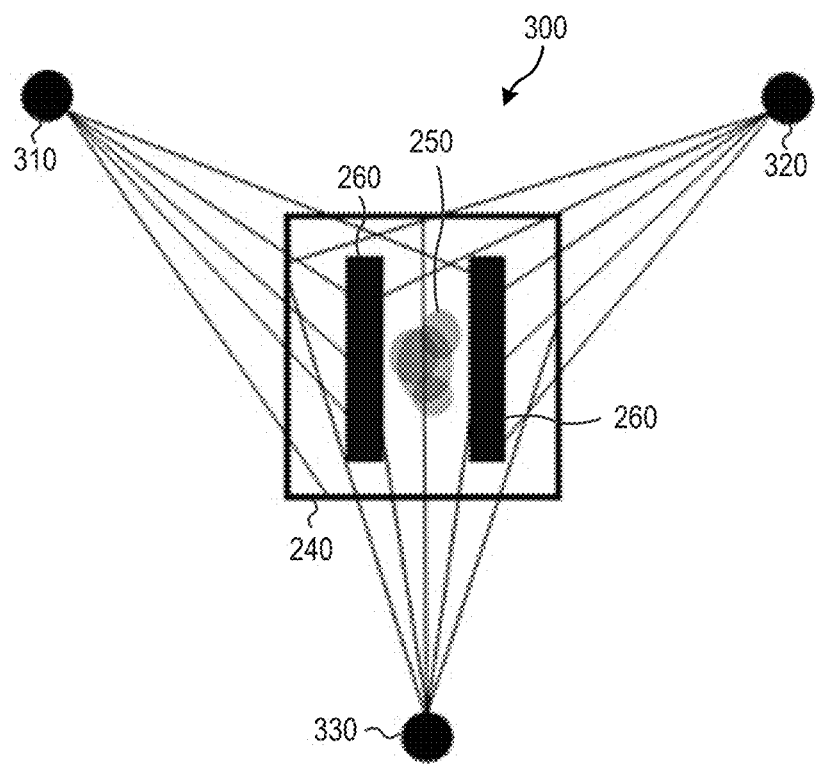
FIG. 3 is an image showing a sparse scan executed from three (3) different viewing locations, according to a disclosed embodiment.

FIG. 3 is an image 300 showing a sparse scan executed from three (3) different viewing locations 310, 320, 330, according to a disclosed embodiment. Again, thin black lines represent the integration path of various concentration measurements. By understanding the occlusion through analysis of spatial data, the viewing locations 310, 320, 330 can be altered to guarantee coverage inside of the vertical bars 260. The plume 250 is correctly interrogated.

Figure 4:
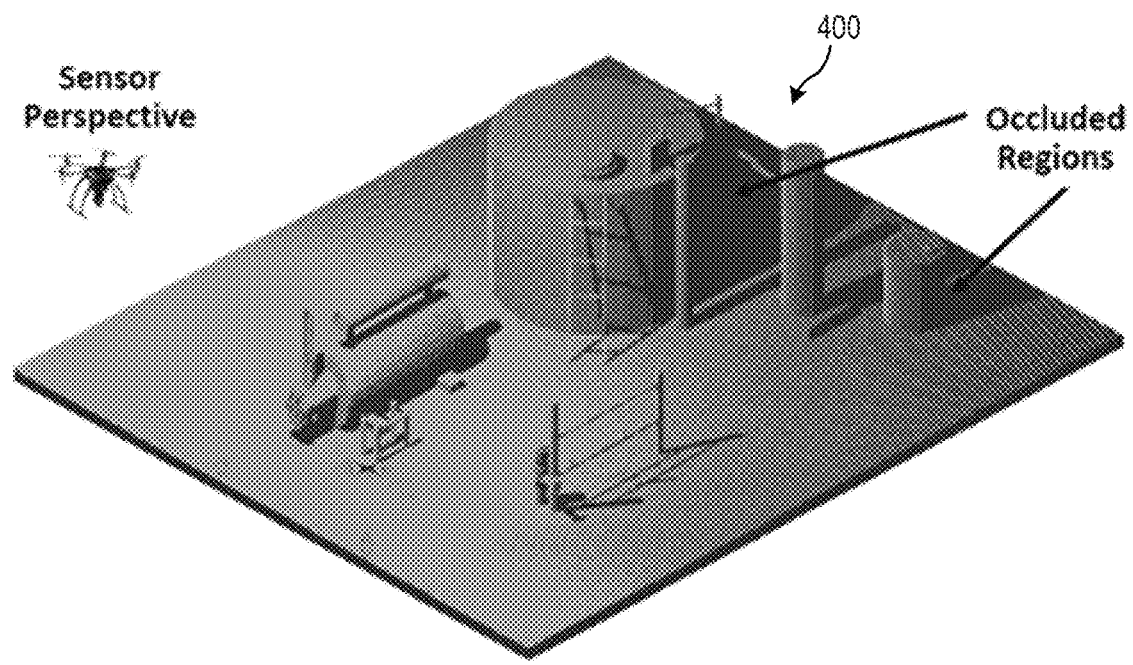
FIG. 4 is an image of the output of an occlusion processing simulation, according to a disclosed embodiment.
Figure 5:
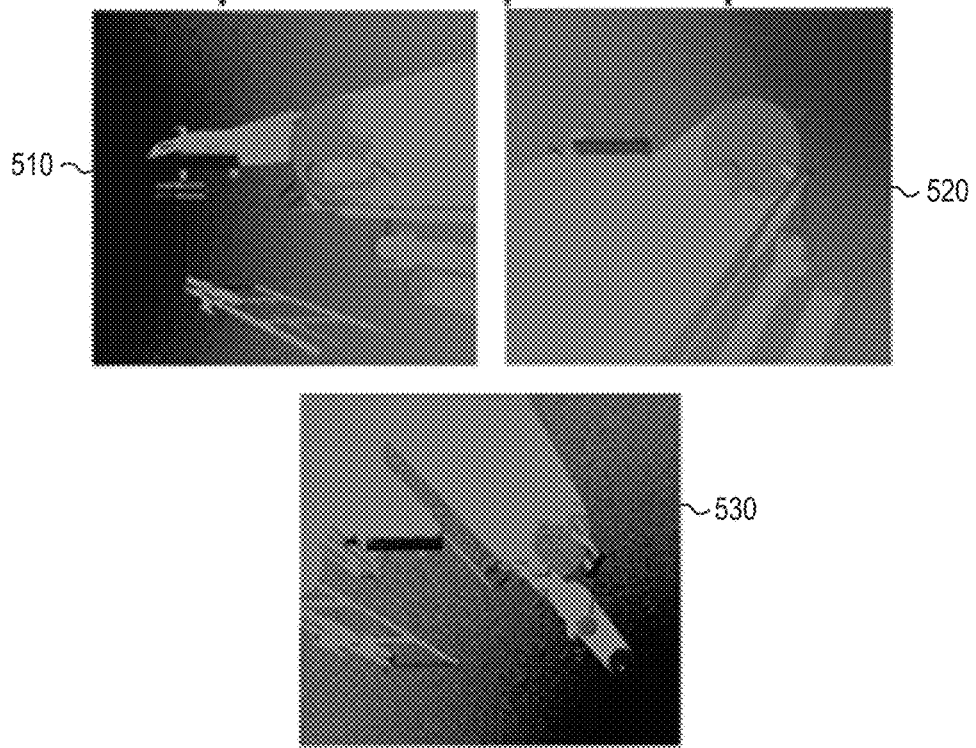
FIG. 5 is a top view of occlusion processing performed from multiple sensor perspectives, according to a disclosed embodiment.

In order to optimize scan positions for maximum coverage, the 3D data may be used to consider the effect of occlusion from an arbitrary viewing location. Line-of-sight algorithms that utilize the 3D spatial data approximate the occlusion effect and can return only points present on non-occluded surfaces from a given viewing location (See, e.g., the Point Cloud Library). These non-occluded points may be termed "viewable surfaces". Implicit in this process is the ability to define which regions of a given volume are also un-occluded or "viewable regions". These regions are defined as the volumetric regions between the viewing location and the viewable surfaces. FIGS. 4 and 5 shows the implementation of this algorithm on a solid model of a mock oil and gas production well pad with the viewable surfaces shaded gray.

FIG. 4 is an image 400 of the output of an occlusion processing simulation. The gray points represent viewable surfaces of the underlying model from the sensor perspective. FIG. 5 is a top view of occlusion processing performed from multiple sensor perspectives 510, 520, 530.

This algorithm can be executed from a variety of viewing locations to provide quantitative estimates of the fraction of the scene that is viewable from each sensor perspective. The 3D spatial data and a collection of possible sensor perspectives can be combined in standard optimization routines (See, e.g., the iminsearch' optimization function in Matlab) to determine number and locations of sensor positions required to view a specified fraction of the measurement scene.

The above discussion demonstrates a basic contribution of 3D data to measurement procedure optimization. However, 3D data presents further opportunities that can be leveraged to accelerate measurement time. In many leak detection cases, certain regions of a scene may be more important than other regions. For example, certain components and/or locations within an infrastructure are more likely to leak. By tailoring measurement procedures to acquire more point density, integration time, or averaging, monitoring areas in close proximity to these components and less measurement resources measuring where such components do not exist, scan time and leak detection probability can be further optimized.

The identification of high probability leak areas may benefit from other or additional 3D spatial data processing. First, segmentation is a robust method for separating 3D data of a structure into its representative parts, components, or elements each defining a contiguous structure (See, e.g., the Point Cloud Library). These constituent elements can then be analyzed as needed in parallel by more complex algorithms. A common segmentation algorithm is called region growing (See, e.g., the Point Cloud Library). Region growing may begin with the generation of a fast nearest-neighbor searchable data structure such as a kd-tree from the 3D spatial data. This data structure supports multiple tasks.

First, surface normal and curvature estimates may be generated. Next, low-curvature "seed" points may be randomly selected. For each seed point, the algorithm may iteratively "grow" a set of points describing a given segment. At each iteration, the algorithm may search the data structure for the nearest neighbors of each point in the set. The nearest neighbors of each point may be appended to the set if they satisfy geometric smoothness constraints based on quantities such as their own curvature or the angular difference in surface normals. The iteration may terminate when no new points are included in the given set. The algorithm may then start again at a new seed. A common stopping condition is that some percentage of the full set of 3D points belongs to one of the segments.

Figure 6:
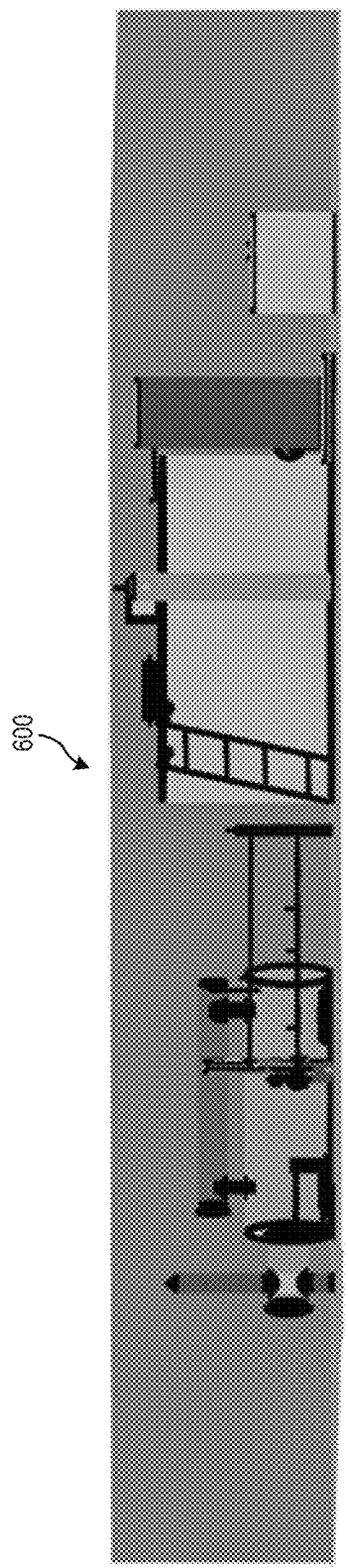
FIG. 6 is an image of an output of a region growing segmentation algorithm showing separation of large objects, according to a disclosed embodiment.

An example output 600 is shown below in FIG. 6. In particular, FIG. 6 is an image 600 of an output of a region growing segmentation algorithm showing separation of large objects (shaded to demonstrate the separation). Borders and smaller complex objects are represented by black points.

In cases where noise on the 3D spatial data degrades the output of the segmentation algorithm, a smoothing and resampling filter such as a moving least squares surface reconstruction can be applied to the data prior to segmentation.

Given the nature of common oil and gas production and distribution infrastructure, two 3D shape "primitives" may be readily exploitable: the plane and the cylinder. Such planes and cylinders of larger sizes and smaller curvatures may be less likely to be sources of gas leaks, and may therefore be identified as less important regions in a scene to scan. By identifying larger and flatter objects that are well represented by such primitives, smaller objects may be isolated, which may make them easier to identify and individually analyze. The region growing algorithm above can be instructed to output large segments. These segments can then be analyzed with basic features such as the distribution of surface normals and basic shape fits to identify them as either planes, cylinders, or "other", as shown in FIGS. 7 and 8.

Figure 7:
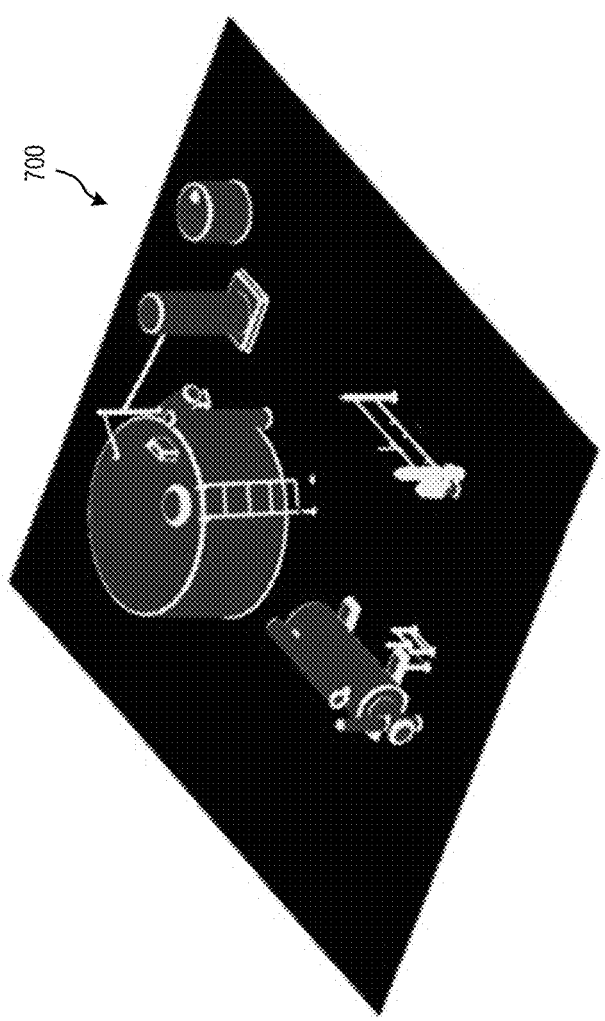
FIG. 7 is an image of the output of a plane/cylinder/other analysis showing localization of the ground (black), large parts (gray) and complex parts (white), according to a disclosed embodiment.

FIG. 7 is an image 700 of the output of a plane/cylinder/other analysis showing localization of the ground (black), large parts (gray) and complex parts (white).

Figure 8:
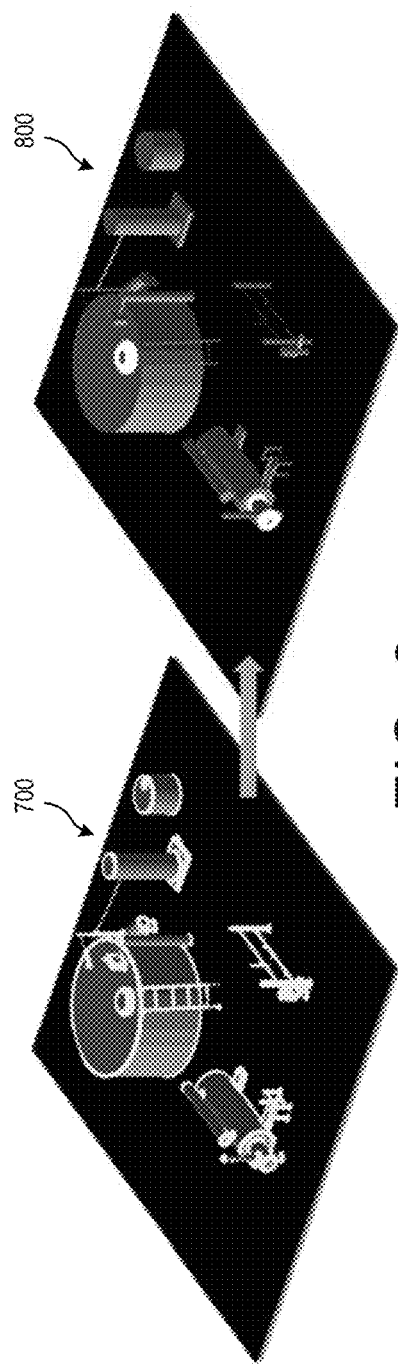
FIG. 8 is a pair of images showing the filtering of segmented 3D spatial data to identify specific components, or components with specific geometric features, according to a disclosed embodiment.

FIG. 8 is a pair of images 700, 800 showing the filtering of segmented 3D spatial data 700 to identify specific components, or components with specific geometric features. In this case the filter selects only cylindrical objects with radii in the intervals 19 cm-21 cm and 30 cm-31 cm. More sophisticated filters can be constructed using spin images, covariance descriptors, point feature histograms, and graph approaches to identify specific components, with nearly arbitrary geometry, within a measurement scene.

The other category may include complex objects such as valves, small pipe clusters, small utility boxes, etc. that are likely leak points. This information can be used to further tailor a measurement procedure to focus, in a non-spatially uniform manner, on these likely leak locations. For a typical well pad scene we have observed that such "high-likelihood" leak points often constitute less than 10% of the surface area of the scene.

The 3D data can afford the ability to further optimize the scan time. 3D shape detection can allow for likely leak sites and large pieces of equipment to be explicitly detected. For instance, with larger, flatter objects identified and removed, the smaller objects can be processed through more advanced shape detection algorithms for specific identification. Commonly used shape identification algorithms include but are not limited to spin images, covariance descriptors, point feature histograms, and graph approaches (See, e.g., A. E. Johnson and M. Hebert, "Using spin images for efficient object recognition in cluttered 3D scenes," IEEE Transactions on Pattern Analysis and Machine Intelligence, vol. 21, no. 5, pp. 433-449, (1999); and D. Fehr, A. Cherian, R. Sivalingam, S. Nickolay, V. Morellas, and N. Papanikolopoulos, "Compact covariance descriptors in 3D point clouds for object recognition," in 2012 IEEE International Conference on Robotics and Automation, pp. 1793-1798, (2012)). Often, the shape identification workflow may be decomposed into pose-invariant feature extraction, which may be followed by classification of the feature space. Training data can be simulated or collected with the 3D topographic imaging system. Once a shape is identified, this information can then be used to incorporate a layer of context that may further define the probability of a leak occurring at that shape, likely constituents of a plume (i.e. methane, water vapor, VOCs, etc.), or possible leak rates. Contextual relationship maps may incorporate the relative position of objects to better identify the objects and to rate their significance. State-of-the-art algorithms refer to this as semantic labeling.

Once identified and rated, high leak probability regions within the 3D spatial data can be combined with wind velocity data to define measurement volumes where detection of gas plumes is likely if a leak is present. An example of this processing step is shown in FIG. 9, and is based on a down-selected set of the well pad components and features identified in FIG. 7.

Figure 9:
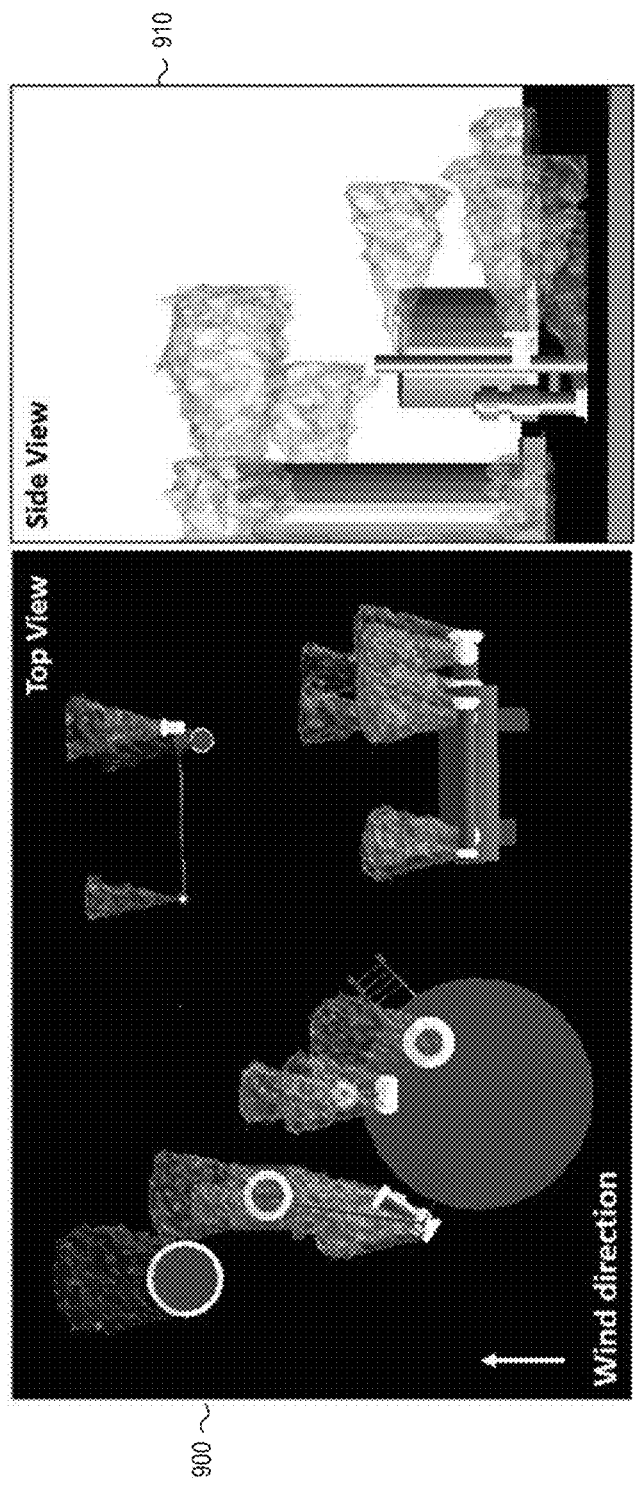
FIG. 9 is a top-view image and a side-view image showing locations of likely-to-leak components (highlighted in white) combined with wind data to define high-probability regions for detecting leaks, illustrated by the transparent gray plume shapes, according to a disclosed embodiment.

FIG. 9 is a top-view image 900 and a side-view image 910 showing locations of likely-to-leak components (highlighted in white) and wind data used to define high-probability regions for detecting leaks, illustrated by the transparent gray plume shapes.

The defined measurement volumes, shaded in gray, occupy less than 5% of the volume and less than 25% of the area—as viewed from above—of the total well pad scene. By heavily weighting the measurement procedure on these regions the measurement time for this scene can be reduced by a factor of 2 to 3. 3D spatial data combined with wind data can facilitate additional specificity and accuracy for defining measurement volumes through the use of computational fluid dynamics (CFD) (See, e.g., online tutorials for the open source computational fluid dynamics software OpenFOAM). Detailed wind velocity fields can be computed for the measurement scene with initial conditions supplied by wind velocity measurements using a variety of CFD programs such as Open FOAM and ANSYS. Wind velocity fields may allow algorithms that define the measurement volumes for a scene to account for more complex gas transport behaviors near objects such as changes in wind speed and direction, backflow regions, and eddy currents.

3. Leak Detection, Localization, Quantification and Source Identification

This section presents methods for combining 3D spatial data with gas concentration measurements to detect, localize and quantify gas leaks and to identify the component corresponding to the leak source.

A first step in this process may be leak detection. A significant problem with existing leak detection methods and technologies is the occurrence of false detection events. Here, 3D spatial data affords substantial benefits over existing state-of-the-art leak monitoring techniques. The ability to compute the path-averaged average gas concentration along a measurement direction can enable extremely sensitive detection of elevated (or otherwise anomalous) gas concentrations, even for gas species with non-zero nominal atmospheric concentrations. Furthermore, the capability to spatially register individual measurements to generate $C_{ave}$ images may allow additional discrimination based on the proximity, continuity and spatial extent of anomalous detections to greatly reduce the probability of false detections. For example, the $C_{ave}$ image in FIG. 10 was created by combining laser ranging distance measurements (3D topography image) with simultaneously acquired path-integrated $CO_2$ concentration measurements. The $C_{ave}$ image shows two $CO_2$ plumes emanating from the ground that leaked from a pipe buried 6' below the surface at a rate of 54 kg/day. A histogram of the $C_{ave}$ image, FIGS. 10 and 11 illustrate the high-sensitivity detection of anomalous $CO_2$ concentrations enabled by this technique.

Figure 10:
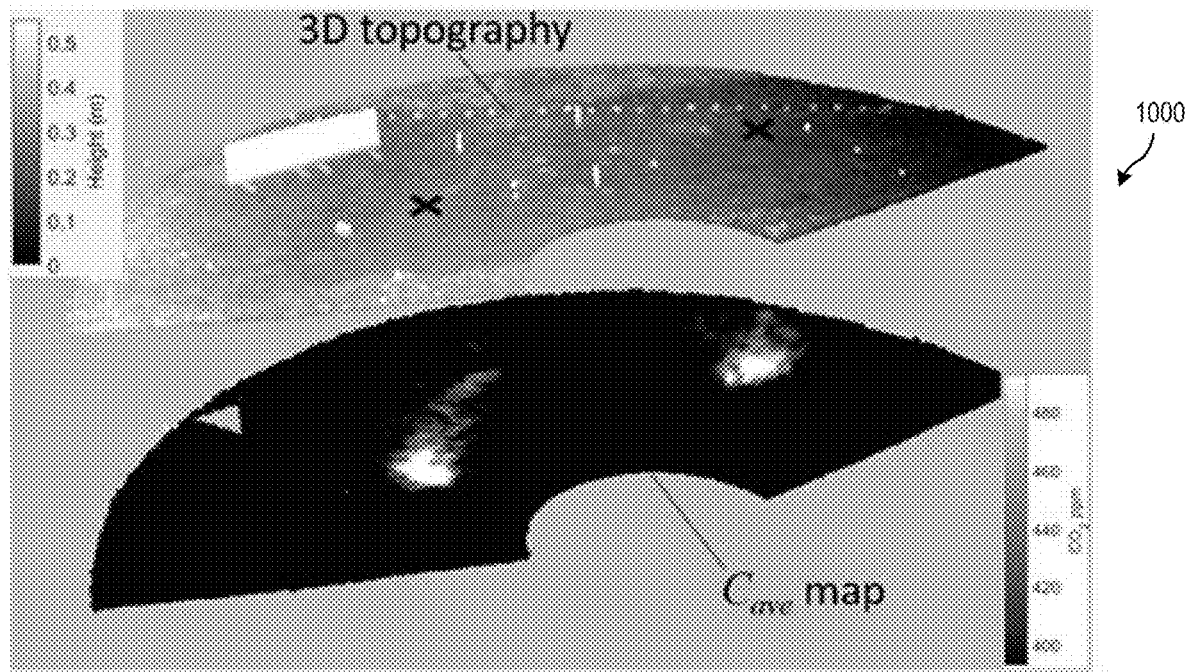
FIG. 10 is a graph of spatially-registered 3D spatial data and gas concentration data. Gas plumes are detected by finding regions in the $C_{ave}$ image containing more than a predefined number of neighboring points exhibiting concentrations exceeding a predefined threshold. The source location for each gas plume, marked by (x) in the 3D topography image, is determined by finding the location of highest anomalous concentration for each contiguous plume, according to a disclosed embodiment.

FIG. 10 is a graph 1000 of spatially-registered 3D spatial data and gas concentration data. Gas plumes are detected by finding regions in the $C_{ave}$ image containing more than a predefined number of neighboring points exhibiting concentrations exceeding a predefined threshold. The determined location of two identified leaks are marked (x) on the 3D spatial image.

Figure 11:
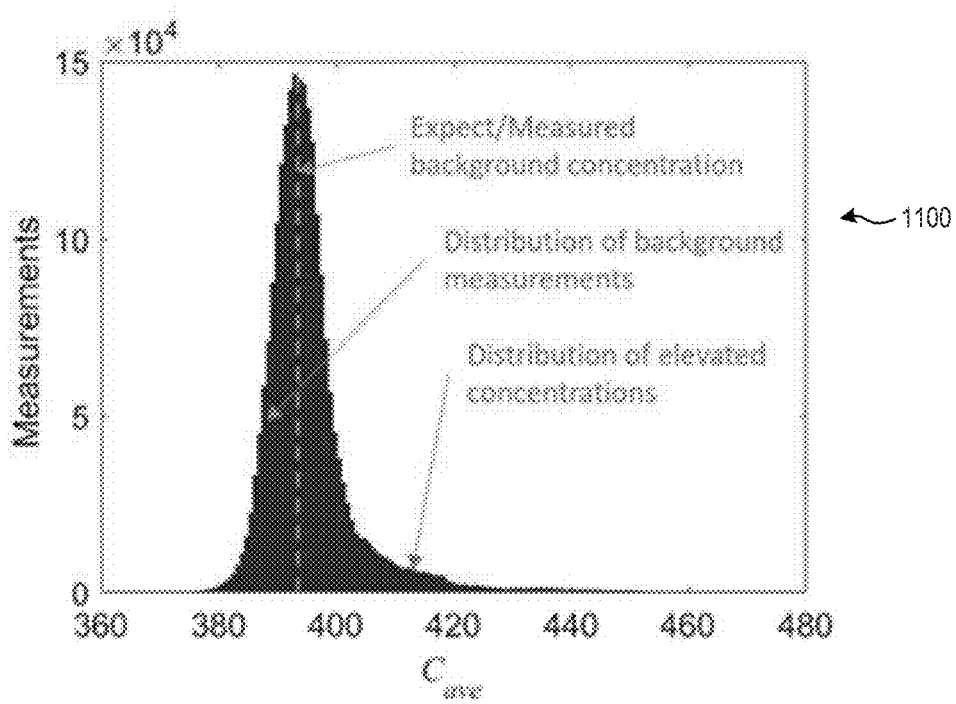
FIG. 11 is a histogram of $C_{ave}$ data showing the expected/measured background concentration and the background and elevated concentration portions of the measurement distribution, according to a disclosed embodiment.

FIG. 11 is a histogram 1100 of the $C_{ave}$ data showing the expected/measured background concentration and the background and elevated concentration portion of the measurement distribution.

The most frequent occurrences in the histogram 1100 corresponds to the nominal atmospheric $CO_2$ background level that covers most of the image. The distribution of background $CO_2$ has a roughly Gaussian shape with 1/e half-width of 5 ppm. The narrow width of the background distribution allows clear distinction between background and elevated measurements that forms the basis of the leak detection and characterization steps presented herein.

An effective algorithm for robust leak detection based on $C_{ave}$ images could have the following steps:

(1) Find points in the image that exceed a predefined concentration threshold for leak detection. Some of these points may be spurious measurements which could cause false positives.

(2) Generate a nearest-neighbor searchable data structure such as a kd-tree from the 3D spatial data.

(3) Search the 3D spatial data to find a predefined number of nearest neighbors surrounding each point identified in step (1).

(4) Query the nearest neighbors found in step (3) to compute the number of neighboring points that also exhibit elevated gas concentration.

(5) Since it is unlikely that spurious measurements would be located near one another spatially, one may report a leak if the number of spatially neighboring points exhibiting elevated concentration exceeds a predefined threshold.

This leak detection algorithm can easily be expanded to discriminate based on additional plume properties, such as spatial extent. Consider a set of points in the $C_{ave}$ image that resulted in a positive leak detection based on steps 1 through 5. A spatial extent threshold for plume detection can be applied by seeding a region growing algorithm at the location of the detected leak, based on concentration, to divide the scene into two segments representing the plume and the rest of the scene. The 3D spatial data can then be used to estimate the area occupied by the detected plume, which can then be compared against a predefined threshold for leak detection. By designing an appropriate set of parameters and thresholds for leak detection, the probability for false detection of a leak can be greatly reduced.

Once a leak has been detected, the 3D spatial data can be leveraged to determine the total quantity of leaked gas in the measurement scene as well as the location of the leak source. As a possible first step, the expected background concentration is subtracted from $C_{ave}$ resulting in an image of the anomalous path-averaged gas concentration within the measurement scene. The expected background level can be estimated from the $C_{ave}$ image (e.g. the centroid of the Gaussian portion of the histogram distribution for the background), or based on supplementary information. As a possible next step, each point within the background-subtracted $C_{ave}$ image may be multiplied by its corresponding target range to form an image of the path-integrated concentration of the anomalous gas ($C_{anom}$) within the measurement scene. As a possible final step, the location of maximum anomalous gas concentration within the $C_{anom}$ image may be designated as the leak source. This location can be determined by a number of methods including Gaussian plume fitting, a gradient search of smoothed $C_{anom}$ data or by implementing a derivative-free optimization algorithm on the $C_{anom}$ image. Further interrogation of the 3D data with occlusion processing can be used to estimate the probability that the leak source resides on a viewable surface. If this step uncovers a significant likelihood that the leak resides on an unviewable surface the 3D data can be used to estimate possible locations of the true leak source. The outcome of this analysis can inform a decision to acquire additional $C_{ave}$ measurements from a different viewing perspective, and provide options for the optimal viewing locations.

After the leak has been located, the 3D data can be leveraged yet again to determine the topographic feature or component at the location of the leak source. As described in the previous section, most object identification procedures rely on layers of contextual information associated with the 3D data. The quantity and detail of the contextual information may dictate the feature identification approach that is best suited for a given measurement case and may determine the specificity of object identification that can be achieved. In cases where limited or no contextual information is available, the 3D data near the leak source can be analyzed via segmentation. An example of this approach is shown in FIG. 13, and is based on co-acquired 3D topography and gas concentration measurements of the scene shown in FIG. 12. First, the location of the gas plume may be determined from the gas concentration image. Next, the surface normals and curvature of the 3D spatial data near the gas plume may be computed and inputted into a region growing algorithm to find regions of high curvature within the measurement scene. The output of this step produces an image segment at the location of the gas plume corresponding to the leak source. The next step can use a piece of contextual information from the measurement scene picture in FIG. 12.

Figure 12:
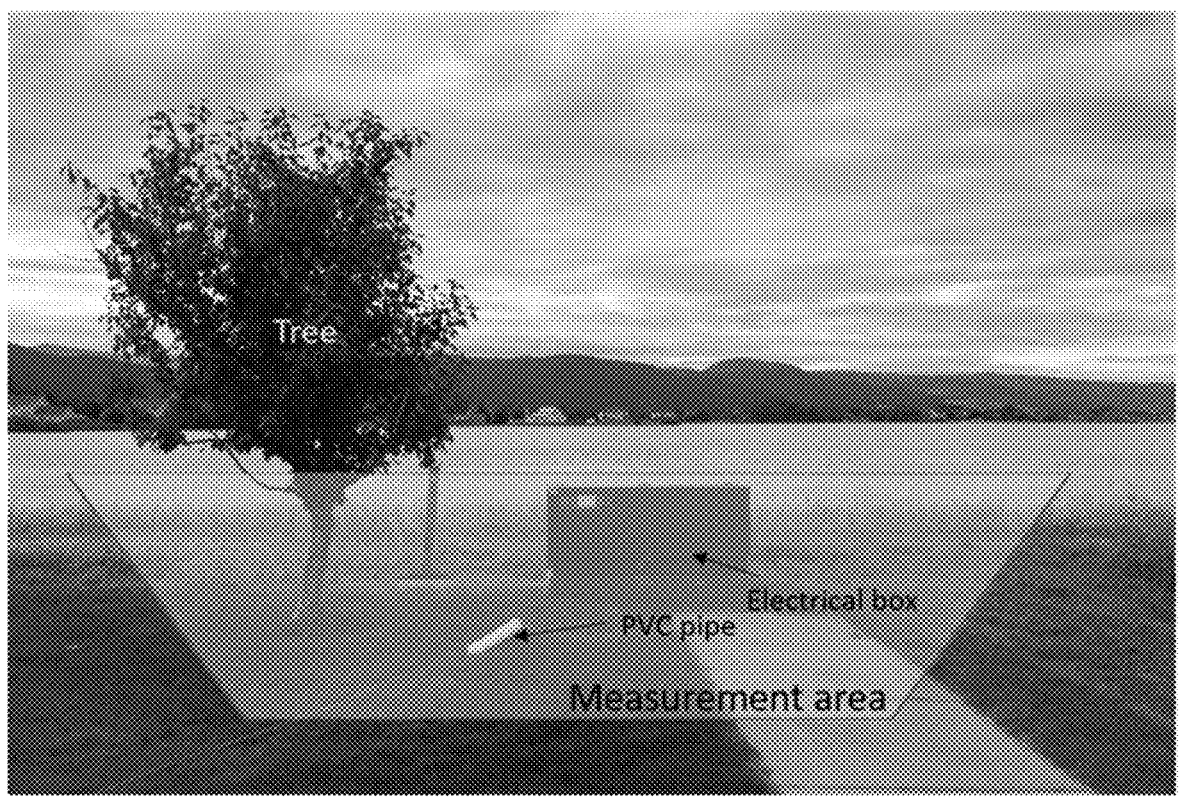
FIG. 12 is a measurement scene used to acquire 3D spatial data and path-averaged $CO_2$ concentration images for the demonstration of leak detection, localization and leaking component identification shown in FIG. 13, according to a disclosed embodiment.
Figure 13:
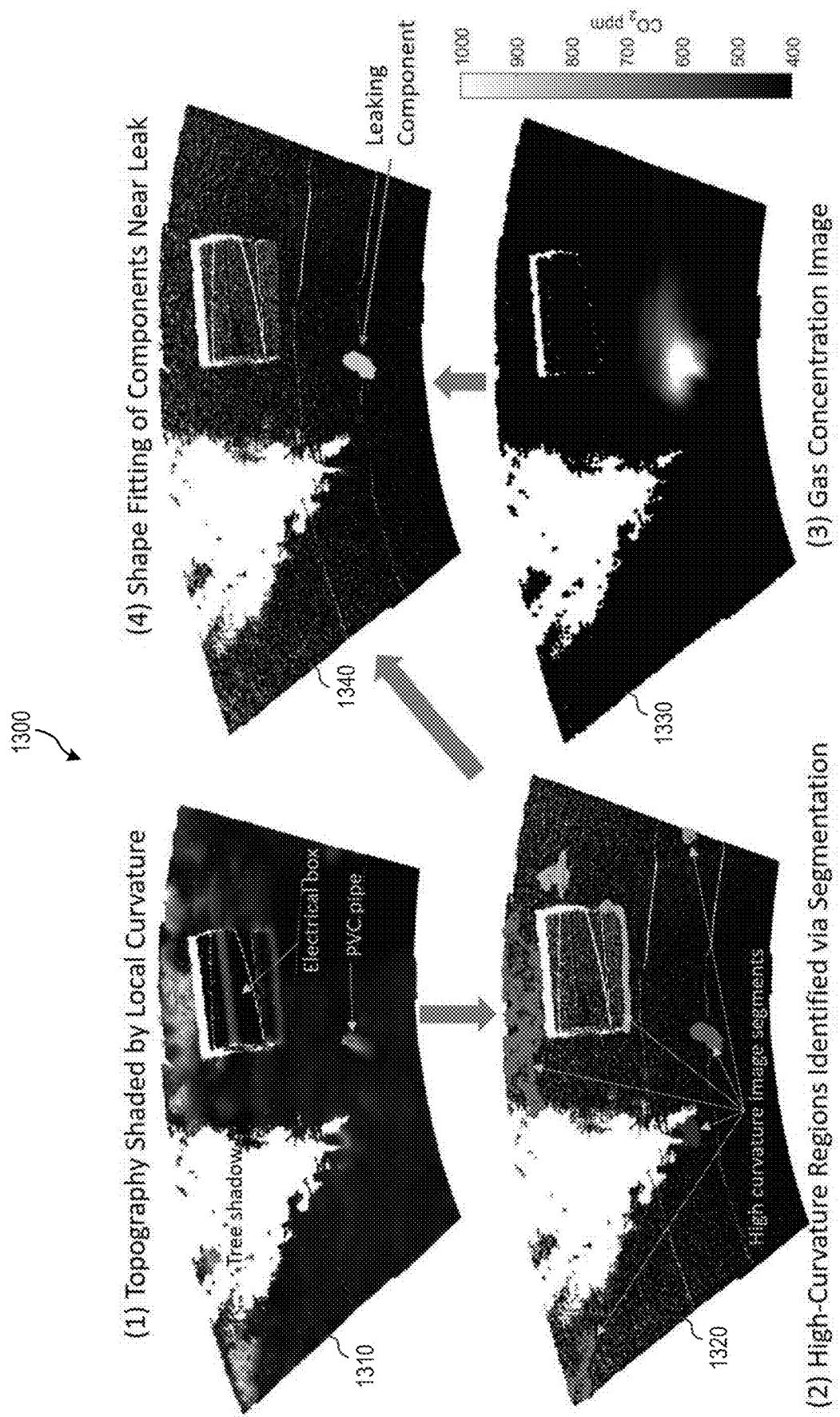
FIG. 13 is a set of images showing example of workflow for leaking component identification, according to a disclosed embodiment.

FIG. 12 is a measurement scene 1200 used to acquire 3D spatial data and path-averaged $CO_2$ concentration images for the demonstration of leak detection, localization and leaking component identification shown in FIG. 13.

FIG. 13 is a set 1300 of images 1310, 1320, 1330, 1340 showing example of workflow for leaking component identification. (1) 3D spatial data acquired via spatially-scanned laser ranging is filtered with a moving least squares filter followed by computation of surface normals and local curvature. (2) A region growing algorithm is used to segment regions of high curvature within the scene. (3) The leak source location is determined using in the gas concentration image. (4) Shape fitting is applied to segmented regions to identify components near the leak location.

The picture shows the object at the leak location that appears to be a pipe with diameter of roughly 4". Using this information a cylindrical shape fit is applied to all image segments identified in FIG. 13 1320 and the segments are ranked based on the residual fit error. The image in FIG. 13 1340 shows the output of a shape fitting filter wherein the pipe, located at the leak source, exhibited the lowest residual shape fit errors.

Object identification can be extremely effective in cases where more contextual information is available. For instance, if the 3D spatial data is geo-registered, the geo-location of the leaking component may be identified through localization of the leak source. In this case, contextual information consisting of a list of components in the scene and their GPS locations may be sufficient to positively identify the leaking component. More sophisticated and generalized object identification can be achieved through shape detection. Here, the 3D data may be used to create a library of components within the measurement scene, and pose-invariant shape detection algorithms may be implemented on sets of measured 3D data to uniquely identify individual components (See, e.g., Karmacharya, A., Boochs, F. & Tietz, B. "Knowledge guided object detection and identification in 3D point clouds." SPIE 9528, 952804-952804-13 (2015)).

The final leak quantification method disclosed herein enables determinations of the rate or flux of a detected leak. To illustrate the approach, an example gas flux measurement performed in a controlled environment is shown in FIGS. 14 and 15.

Figure 14:
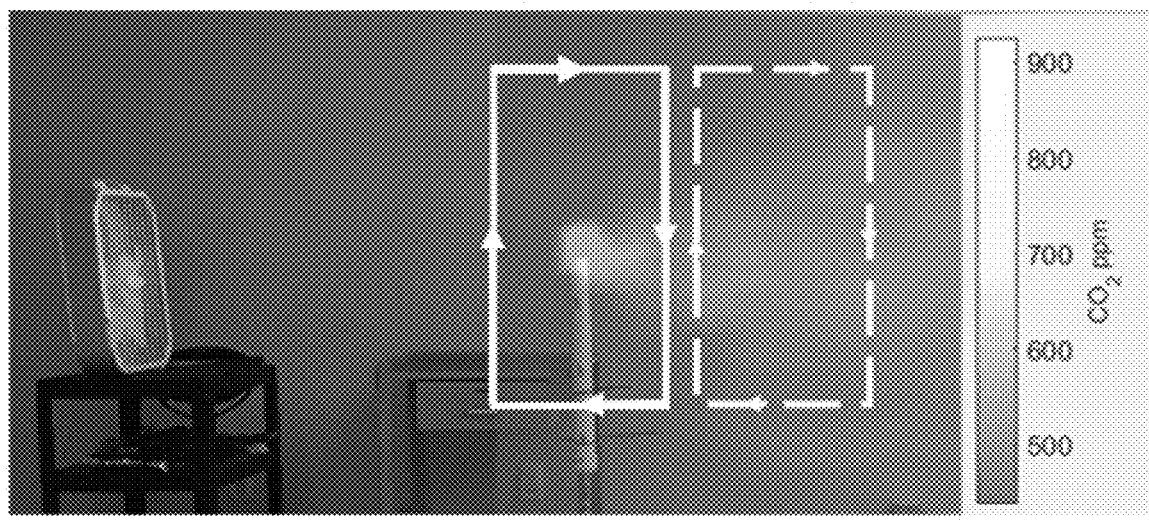
FIG. 14 is a diagram showing a setup for demonstration of gas imager flux measurements including a pipe emitting $CO_2$ at a rate regulated by a mass flow controller, a fan to simulate wind, according to a disclosed embodiment.

FIG. 14 is a diagram 1400 showing a setup for demonstration of gas imager flux measurements including a pipe emitting $CO_2$ at a rate regulated by a mass flow controller and a fan to simulate wind. Scan patterns used for flux measurements are indicated by dashed-white and solid white lines.

Figure 15:
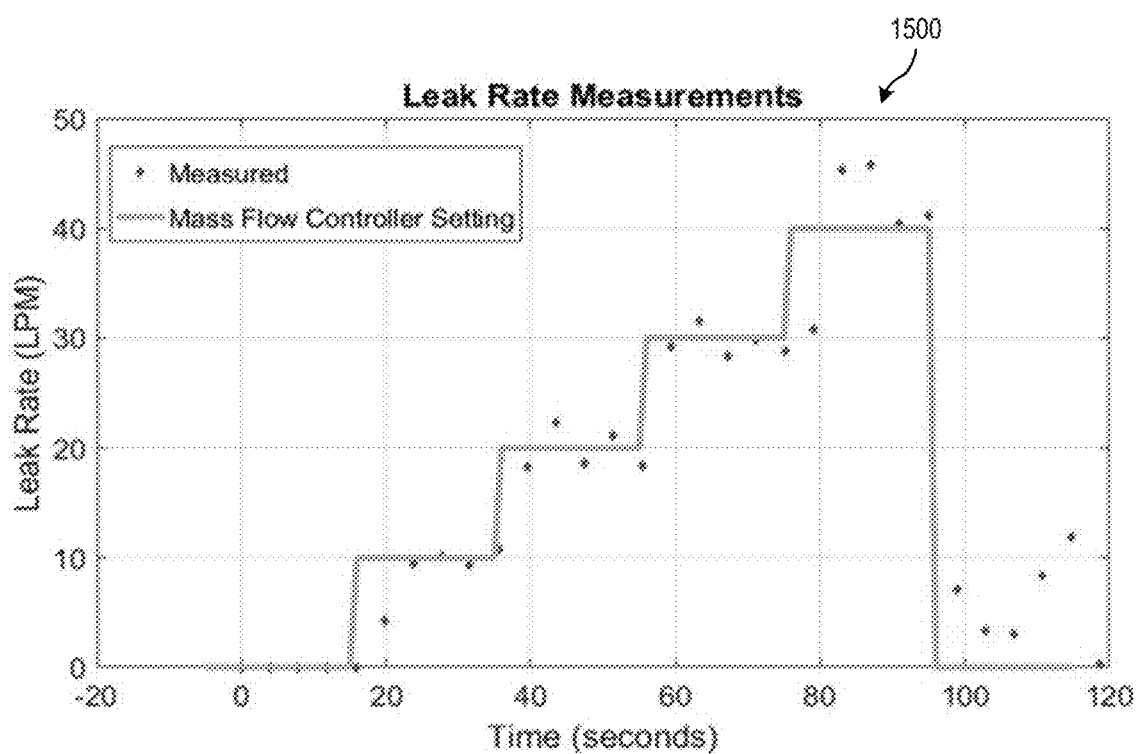
FIG. 15 is a graph showing flux measurements of $CO_2$ performed using Gaussian plume fitting and simultaneous acquisition of target range and integrated-path gas concentration measurements along the dashed-white scan path of FIG. 14, according to a disclosed embodiment.

FIG. 15 is a graph 1500 showing flux measurements of $CO_2$ performed using Gaussian plume fitting and simultaneous acquisition of target range and integrated-path gas concentration measurements along the dashed-white scan path of FIG. 14.

The picture in FIG. 14 shows the measurement scene consisting of a vertical pipe that emits $CO_2$ at a rate determined by a mass flow controller. A fan is positioned near the leak source to simulate wind, and a 2-dimensional anemometer was used to measure the wind velocity, roughly 1 m/s, at the leak source. Prior to flux rate estimation, high-resolution 3D topography and gas concentration images of the leak area were acquired to determine the location and extent of the gas plume, and to inform the choice of leak rate scan pattern.

The high-resolution plume image and two possible scan patterns for leak rate estimation are overlaid on the measurement scene picture in FIG. 14. The two scan patterns are designed to optimize different aspects of the flux measurement. Both patterns transect the plume in a direction approximately perpendicular to the flow. This can be important since perpendicular transects may produce the lowest noise flux measurements due to fluctuations in the wind velocity and plume concentration. Both patterns also form a closed volume between the sensor and the target surface, such that no gas can enter or escape the enclosed volume without passing through the measurement beam. The two patterns differ in that one encloses the leak source, while the other transects the plume twice at different distances from the leak source. Enclosing the leak source may be desirable because it can enable discrimination between gas sources originating within the enclosed scan pattern from those located outside the scan pattern. A leak-enclosing pattern may be favored in situations where multiple gas sources are present in the measurement scene. On the other hand, the scan that transects the plume twice may enable estimation of the gas velocity, even without an independent wind measurement, via temporally correlating plume parameters at the two transect locations. This method for estimating gas velocity is akin to block matching techniques used to estimate flux from camera-based gas absorption images (See, e.g., Sandsten, J., et. al., "Volume flow calculations of gas leaks imaged with infrared gas-correlation." Opt. Exp., 20, 20318-20329 (2012)). Plume parameters that can be temporally correlated to estimate wind data at spatially separated transect locations include the plume centroid location, plume shape and plume concentration.

To estimate the gas flux (Q), the plume transect measurements can be fit with Gaussian plume model, $$C = \frac{Q}{2\pi u \sigma_y \sigma_z} e^{\frac{-y^2}{2\sigma_z^2}} \left[ e^{\frac{-(z-H)^2}{2\sigma_z^2}} + e^{\frac{-(z+H)^2}{2\sigma_z^2}} \right], \quad (2)$$

where C is the gas concentration as a function of spatial coordinates y and z, u is the gas velocity, $\sigma_y$ and $\sigma_z$ are the standard deviations of the plume distribution in the y and z directions and H is the plume centroid in the z-direction.

The measurements in FIG. 15 were acquired with the dashed scan pattern at a rate of 4 scans per second, and analyzed with Gaussian plume fitting. Eight individual transect measurements were averaged yielding updated flux estimates at 2 second intervals. Over the course of 120 seconds the mass flow rate of $CO_2$ was stepped in intervals of 10 liters per minute from 0 lpm to 40 lpm and back to 0 lpm. The measured $CO_2$ flux estimates show good agreement with the mass controller settings for this test consistently registering within 10% of the set value at each step. Another way to estimate the gas flux Q is to multiply the gas speed by the integrated anomalous gas concentration along the plume transect. In this case the flux estimate is given by, $$Q = u \Sigma_i^N C_{anom} \Delta y, \quad (3)$$

where N is the number of $C_{anom}$, measurements along the plume transect and $\Delta y$ is the spacing between $C_{anom}$, measurements at the location of the plume. This method has the benefit that it does not require fitting and it works for plumes of any shape.

A requirement for accurate estimates of the gas flux (Q) may be knowledge of the distance from the sensor to the gas plume for proper scaling of the spacing between $C_{anom}$ measurements $\Delta y$ or the plume standard deviations, $\sigma_y$ and $\sigma_z$, depending on the estimation technique being used. Such information may be difficult to ascertain from a single measurement perspective because a plume with small $\sigma_y$ and $\sigma_z$ located close to the sensor can appear similar in gas concentration imagery as a plume with large $\sigma_y$ and $\sigma_z$ located farther from the sensor. The situation is simplified for the measurement scenario in FIG. 14 as the flux measurement is performed close to the pipe emitter, and the range from the sensor to the pipe is measured in the 3D topography data. In cases where the plume is located further from surfaces in the measurement scene it may be necessary to localize the plume within the measurement volume to get an adequate estimate of the distance from the sensor to the plume transect being analyzed. Volumetric localization can be accomplished by measuring the plume from more than one perspective, and performing gas absorption tomography (See, e.g., Twynstra, M. G. and Duan, K. J., "Laser-absorption tomography beam arrangement optimization using resolution matrices," Applied Optics, 29, 7059-7068 (2012)). An example of tomography for plume localization is shown in FIGS. 16-18.

Figure 16:
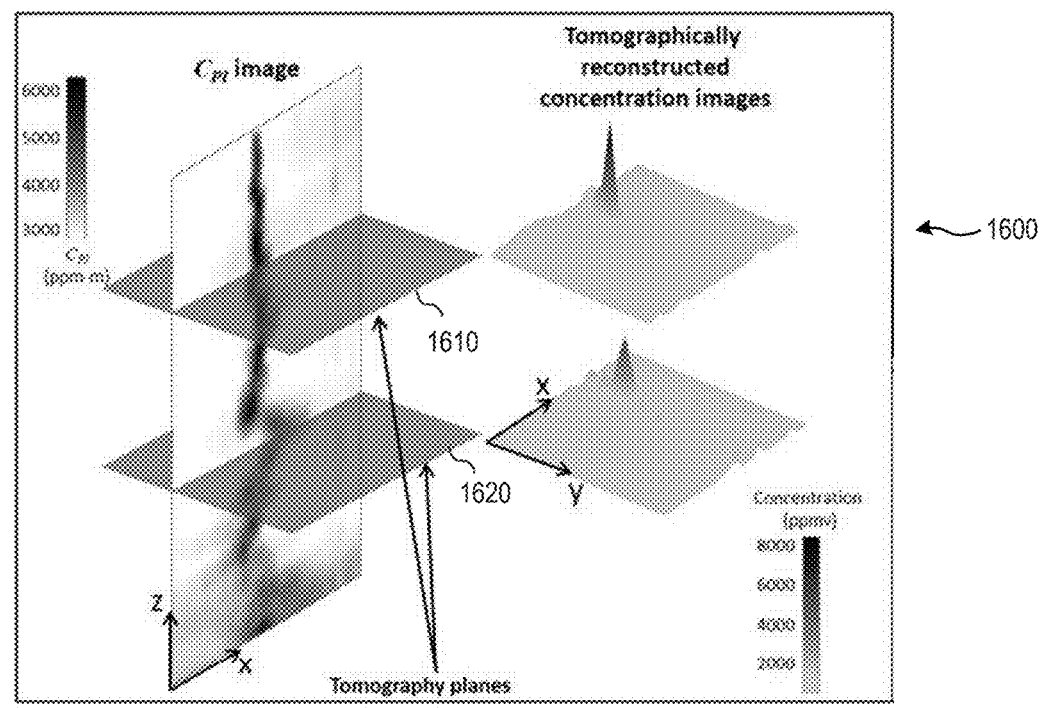
FIG. 16 is an image of a path-integrated gas concentration image indicating the locations of two planes used for tomographic reconstruction of concentration images, according to a disclosed embodiment.

FIG. 16 is an image 1600 of a path-integrated gas concentration image indicating the locations of two planes 1610, 1620 used for tomographic reconstruction of concentration images. The reconstructed concentration imagers have 0.3 m voxel resolution in the x and y dimensions. Resolution in the z dimension depends on the density of reconstructed planes.

Figure 17:
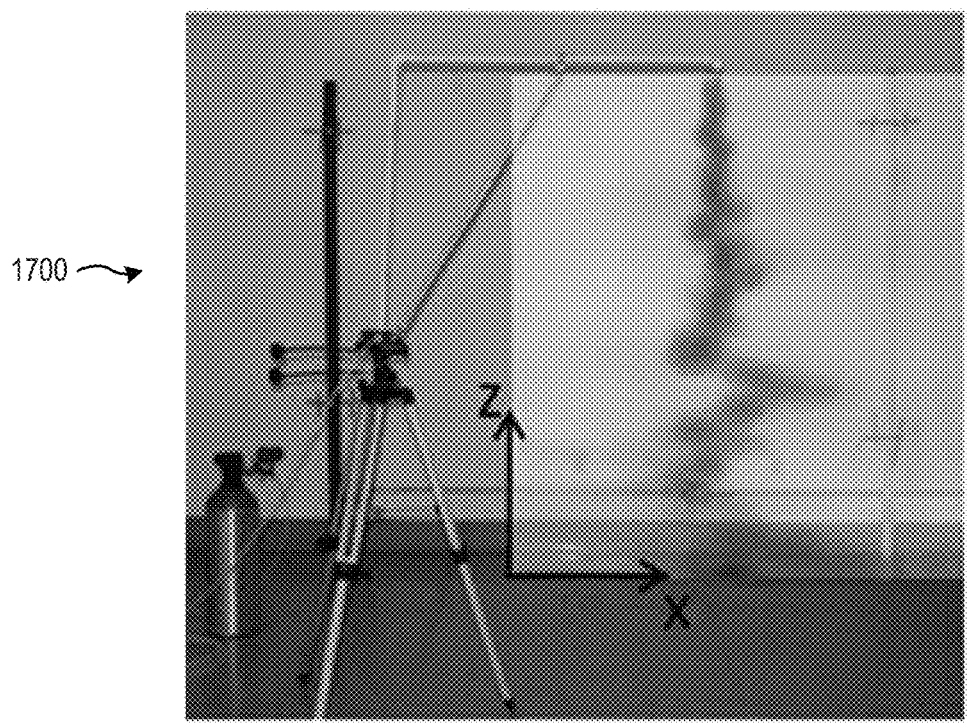
FIG. 17 is a picture of the measurement scene containing the '$CO_2$ shower' with an overlaid path-integrated gas concentration image, according to a disclosed embodiment.

FIG. 17 is a picture 1700 of the measurement scene containing the 'CO$_2$ shower' with an overlaid path-integrated gas concentration image.

Figure 18:
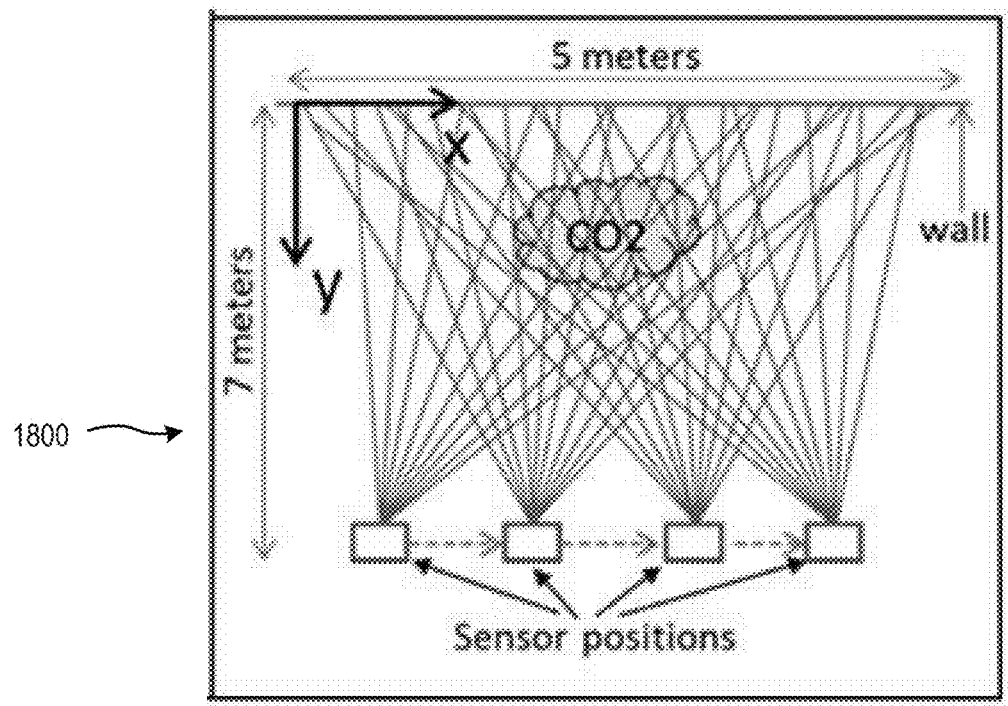
FIG. 18 is a schematic of the measurement geometry of FIG. 17, according to a disclosed embodiment.

FIG. 18 is a schematic 1800 of the measurement geometry of FIG. 17. Tomographic CO$_2$ concentration reconstructions are enabled by combining path-integrated CO$_2$ concentration measurements and target range measurements from multiple sensor positions.

FIG. 17 shows the measurement scene with an overlaid CO$_2$ concentration image of a plume falling from an elevated pipe. FIG. 18 provides a schematic of the sensor positions from which subsequent coarse resolution scans of the plume are performed. Coarse spatial resolution measurements may be used for plume tomography so measurements from multiple perspectives can be acquired before the plume location changes appreciably. FIG. 16 shows tomographic reconstructions of the plume at two transects that result in determinations of the y-direction distance to the plume from the sensor at each transect. In general, the tomographic reconstruction of gas concentration may be performed by superposing a grid of N cells on the reconstruction plane and inverting the equation, $$b_i = \Sigma_j^N A_{ij} x_j, \quad (4)$$

where $b_i$ is the molar fraction integrated-path gas concentration measurement along the $i^{th}$ measurement direction, $A_{ij}$ is the chord length along the $i^{th}$ direction inside the $j^{th}$ grid cell and $x_j$ is the molar fraction gas concentration in the $j^{th}$ grid cell. With spatially coarse measurements it can be difficult to acquire sufficient concentration measurements ($b_i$) to invert equation 4 directly. Conversely, taking the time to acquire higher spatial resolution gas measurements at many sensor positions can allow the plume position to evolve during the measurement, which also hinders tomographic reconstruction. This problem can be overcome by rapidly acquiring coarse spatial resolution measurements and applying one of a number of techniques for spanning the null space of the under-sampled reconstruction grid. Examples include Tikihonov regularization, interpolation of the concentration measurements ($b_i$) or Gaussian fitting of the plumes measured from each position (See, e.g., Twynstra, M. G. and Duan, K. J., "Laser-absorption tomography beam arrangement optimization using resolution matrices," Applied Optics, 29, 7059-7068 (2012)).

In summary, the methods for leak detection and characterization disclosed herein enable the determination of the leak location, leak quantification, and identification of equipment that is the likely leak source. As the source of the leak may be a surface in the scene, the search procedure can be greatly accelerated with the use of 3D spatial data. Equipment or features identified in the 3D spatial data can be ranked according to likelihood as a leak source to define efficient measurement procedures. When a leak is detected and localized, the 3D information can be compared to the location of the detected plume and the environmental conditions (i.e. wind direction) to quickly identify the most likely leak sources. Elevated gas concentration near the possible leak source can confirm or deny each hypothesis. Once a specific leak site is identified, the system can follow up with gas quantification measurements and a high-resolution measurement of the equipment demonstrating the leak. This process can give site managers actionable information. For example, a dispatch engineer may know which part needs to be repaired or replaced before ever visiting the site.

We claim:

1. A method, comprising:
identifying a first occluded volumetric region of a physical scene that is occluded from a first viewpoint based on 3D spatial data, the 3D spatial data having 3D coordinates of physical points associated with a plurality of surfaces that are viewable from the first viewpoint;
identifying a second viewpoint of the physical scene for which at least portion of the first occluded volumetric region is not occluded from view;
performing a first gas sensing measurement based on the first viewpoint; and
performing a second gas sensing measurement based on the second viewpoint.

2. The method of claim 1, further comprising:
determining, a location of a gas leak source based, at least in part, on the first or second gas sensing measurements.

3. The method of claim 2, further comprising:
determining a physical component corresponding to the gas leak source.

4. The method of claim 1, further comprising:
performing occlusion processing on the 3D spatial data.

5. The method of claim 1 wherein
the identification of the first occluded volumetric region includes segmentation of structures or features in the 3D spatial data.

6. The method of claim 1 wherein
the identification of the first occluded volumetric region includes shape detection or feature identification of structures or features in the 3D spatial data.

7. The method of claim 1 further comprising:
performing the first or second gas sensing measurements with a mobile gas sensor.

8. The method of claim 1, further comprising:
determining an anomalous gas quantity in the physical scene that is greater or less than the background gas quantity in the physical scene based, at least in part on the first or second gas sensing measurements.

9. The method of claim 8 wherein
the determined anomalous gas quantity is calculated by first subtracting the background path-averaged gas concentration that is either measured or otherwise known to be in the scene from the measured path-averaged gas concentration data to derive path-integrated anomalous gas concentration data, the path-integrated anomalous gas concentration data is then integrated over the spatial coordinates of the measurement scene to determine the anomalous gas quantity.

10. The method of claim 1, wherein
the first or second gas sensing measurements form, at least in part, a plurality of viewing locations that are used to reduce the occurrence of undetected leaks within the physical scene.

11. The method of claim 1, further comprising: determining a location of a gas plume in 3D space by combining the 3D spatial data with gas data from, at least in part, the first or second gas sensing measurements using a tomographic reconstruction algorithm.

* * * * *